(12) United States Patent
Chen

(10) Patent No.: US 8,951,529 B2
(45) Date of Patent: Feb. 10, 2015

(54) METHODS OF USING SMALL COMPOUNDS TO ENHANCE MYELOID DERIVED SUPPRESSOR CELL FUNCTION FOR TREATING AUTOIMMUNE DISEASES

(75) Inventor: Shu-Hsia Chen, New York, NY (US)

(73) Assignee: Icahn School of Medicine at Mount Sinai, New York, NY (US)

(*) Notice: Subject to any disclaimer, the term of this patent is extended or adjusted under 35 U.S.C. 154(b) by 0 days.

(21) Appl. No.: 13/518,513

(22) PCT Filed: Dec. 21, 2010

(86) PCT No.: PCT/US2010/061610
§ 371 (c)(1),
(2), (4) Date: Dec. 11, 2012

(87) PCT Pub. No.: WO2011/087795
PCT Pub. Date: Jul. 21, 2011

(65) Prior Publication Data
US 2013/0108579 A1 May 2, 2013

Related U.S. Application Data

(60) Provisional application No. 61/289,218, filed on Dec. 22, 2009.

(51) Int. Cl.
| | | |
|---|---|---|
| A61K 38/02 | (2006.01) | |
| A61K 35/14 | (2006.01) | |
| A61K 31/137 | (2006.01) | |
| A61K 31/395 | (2006.01) | |
| A61K 31/416 | (2006.01) | |
| A61K 31/465 | (2006.01) | |
| A61K 38/18 | (2006.01) | |
| A61K 38/19 | (2006.01) | |

(52) U.S. Cl.
CPC ............... *A61K 38/02* (2013.01); *A61K 31/137* (2013.01); *A61K 31/395* (2013.01); *A61K 31/416* (2013.01); *A61K 31/465* (2013.01); *A61K 38/18* (2013.01); *A61K 38/193* (2013.01); *A61K 35/15* (2013.01)
USPC ..................... 424/184.1; 424/85.1; 424/278.1

(58) Field of Classification Search
None
See application file for complete search history.

(56) References Cited

U.S. PATENT DOCUMENTS

| | | |
|---|---|---|
| 2004/0136973 A1* | 7/2004 | Huberman et al. ........ 424/93.21 |
| 2004/0186052 A1 | 9/2004 | Iyer et al. |
| 2005/0136103 A1 | 6/2005 | Ben-Sasson et al. |
| 2009/0269302 A1 | 10/2009 | Salfeld et al. |
| 2011/0059106 A1 | 3/2011 | Kuchroo et al. |

OTHER PUBLICATIONS

Cuenca et al (Mol Med. Mar.-Apr. 2011;17(3-4):281-92. Epub Nov. 12, 2010).*
Bowen et al (J Immunol. Dec. 1, 2009;183(11):6971-80. Epub Nov. 4, 2009).*
Ma (Modern Drug Discovery 2004, 7(6)).*
An International Preliminary Report on Patentability mailed Jun. 26, 2012, which issued in corresponding International Application No. PCT/US2010/061610.
Aharoni et al. "The therapeutic effect of glatiramer acetate in murine model of inflammatory bowel disease is mediated by anti-inflammatory T-cells" *Immunology Letter* (2007) 112 110-119.
Aharoni et al. "Copolymer 1 induces T cells of the T helper type 2 that crossreact with myelin basic protein and suppress experimental autoimmune encephalomyelitis" *Proc Natl Acad Sci USA* (1997); vol. 94:10821-6.
Almand et al. "Increased Production of Immature Myeloid Cells in Cancer Patients: A Mechanism of Immunosuppression in Cancer" J Immunol. (2001) 166:678-689.
Apolloni et al "Immortalized Myeloid Suppressor Cells Trigger Apoptosis in Antigen-Activated T Lymphocytes" *J. Immunol.* (2000) 165:6723-6730.
Autschbach et al. "Cytokine/chemokine messenger-RNA expression profiles in ulcerative colitis and Crohn's disease" *Virchows Arch.* (2002) 441:500-13.
Bennett et al. "SP600125, an anthrapyrazolone inhibitor of Jun N-terminal kinase" *Proc Natl Acad Sci U S A.* (2001) 98:13681-13686.
Bronte et al. "Identification of a CD11b$^+$/Gr-1$^+$/CD31$^+$ myeloid progenitor capable of activating or suppressing CD8$^+$ cells" *Blood* (2000) 96:3838-46.
Bronte et al. "IL-4-Induced Arginase 1 Suppresses Alloreactive T Cells in Tumor-Bearing Mice" *J Immunol.* (2003) 170:270-278.
Bronte et al. "Unopposed Production of Granulocyte-Macrophage Colony-Stimulating Factor by Tumors Inhibits CD8$^+$ T Cell Responses by Dysregulating Antigen-Presenting Cell Maturation" *J. Immunol.* (1999) 162:5728-5737.
Bronte et al. "L-arginine metabolism in myeloid cells controls T-lymphocyte functions" *Trends Immunol.* (2003) 24:301-305.
Brooks et al. "The Inhibitory Effect of Cyclophosphamide-Induced MAC-1$^+$ Natural Supressor Cells on IL-2 and IL-4 Utilization in MLR" *Transplantation.* (1994) 58:1096-1103.
Cao et al. "Delivering neuroactive molecules from biodegradable microspheres for application in central nervous system disorders" *Biomaterials* (1999) (4):329-39.
Caspi et al. "The Association of Inflammatory Bowel Disease and Leukemia-Coincidence or Not" *Leukemia & Lymphoma* (1995) vol. 17, No. 3-4, pp. 255-262.
Cheng et al "Inhibition of dendritic cell differentiation and accumulation of myeloid-derived suppressor cells in cancer is regulated by S100A9 protein" *J. Exper. Med.* vol. 205, No. 10, 2235-2249.

(Continued)

*Primary Examiner* — Brian J Gangle
*Assistant Examiner* — Andrea McCollum
(74) *Attorney, Agent, or Firm* — Fish & Richardson P.C.

(57) ABSTRACT

Methods for enhancing the suppressive function of myeloid derived suppressor cells (MDSCs) for the treatment of autoimmune diseases using small compounds are disclosed. In certain aspects, the small compounds are glatiramer acetate and mitogen activated protein (MAP) kinase inhibitors. In other aspects, these methods include the administration of exogenous MDSCs or the use of endogenous MDSCs mobilized using stem cell mobilizers. In yet other aspects, compositions containing MDSCs and small compounds of the invention are provided.

8 Claims, 28 Drawing Sheets

(56) References Cited

OTHER PUBLICATIONS

Childs et al. "Engraftment Kinetics After Nonmyeloabiative Allogeneic Peripheral Blood Stem Cell Transportation: Full Donor T-Cell Chimerism Precedes Alloimmune Responses" *Blood* (1999), 94:3234-3241.

Disis et al. "Flt3 ligand as a vaccine adjuvant in association with HER-2/neu peptide-based vaccines in patients with HER-2/neu-overexpressing cancers" *Blood*. (2002) 99: 2845-2850.

Dombret et al. "De nono acute myeloid leukemia in patients with Crohn's Disease" *Nouv Rev Fr Hematol*. (1995) 37(3):193-6.

Ferrara et al. "Graft-versus-Host Disease" *N. Engl. J Med.* (1991) 324:667-674.

Flomenberg et al. "The use of AMD3100 plus G-CSF for autologous hematopoietic progenitor cell mobilization is superior to G-CSF alone" *Blood* (2005) 106(5):1867-1874.

Horowitz et al. "Graft-Versus-Leukemia Reactions After Bone Marrow Transplantation" *Blood*. (1990) 75:555-562.

Huang, et al. "Gr-1+CD115+Immature Myeloid Suppressor Cells Mediate the Development of Tumor-Induced T Regulatory Cells and T-cell Anergy in Tumor-Bearing Host" *Cancer Res.* (2006) 66: 1123-1131.

Johnson et al. "Copolymer 1 reduces relapse rate and improves disability in relapsing-remitting multiple sclerosis" *Neurology* (1995) 45:1268-1276.

Kawada et al. "Insights from advances in research of chemically induced experimental models of human inflammatory bowel disease" *World J. Gastroenterol.* (2007) 13: 5581-5593.

Kawai et al. "TLR signaling" *Semin Immunol* (2007) 19:24-32.

Kimura et al. "The sphingosine 1-phosphate receptor agonist FTY720 supports CXCR4-dependent migration and bone marrow homing of human CD34+ progenitor cells" *Blood* (2004) 103(12):4478-4486.

Kusmartsev et al. "All-*trans*-Retinoic Acid Eliminates Immature Myeloid Cells from Tumor-bearing Mice and Improves the Effect of Vaccination" *Cancer Res.* (2003) 63:4441-4449.

Kusmartsev et al. "Functional Characteristics of Bone Marrow Immune Suppressive Cells in Patients with Gastric Canser" *Int. J Immunopathol. Pharmacol.* (1998), 11: 171-178.

Kusmartsev et al. "Gr-1+ Myeloid Cells Derived from Tumor-Bearing Mice Inhibit Primary T Cell Activation Induced Through CD3/CD28 Costimulation" *J. Immunol.* (2000) 165:779-785.

Kusmartsev et al. "Antigen-Specific Inhibition of CD8+ T Cell Response by Immature Myeloid Cells in Cancer Is Mediated by Reactive Oxygen Species" *J. Immunol.* (2004) 172: 989-999.

Langer "New Methods of Drug Delivery" *Science* (1990) 249:1527-1533.

Larochelle et al. "AMD3100 mobilizes hematopoietic stem cells with long-term repopulating capacity in nonhuman primates" *Blood* (2006) vol. 107 (9):3772-3778.

Li et al. "Role of Immature Myeloid Gr-1+ Cells in the Development of Antitumor Immunity" *Cancer Res.* (2004) 64:1130-1139.

Li et al. "Cancer-Expanded Myeloid-Derived Suppressor Cells Induce Anergy of NK Cells through Membrane-Bound TGF-β1" *J Immunol.* (2009) 182, 240-249.

Liles et al. "Mobilization of hematopoietic progenitor cells in healthy volunteers by AMD3100, a CXCR4 antagonist" *Blood* (2003) 102(8):2728-2730.

Mazzoni et al. "Myeloid Suppressor Lines Inhibit T Cell Responses by an NO-Dependent Mechanism" *J. Immunol.* (2002) 168:689-695.

Medzhitov Recognition of microorganisms and activation of the immune response: *Nature* (2007) 449:819-26.

Murthy et al. "Treatment of Dextran Sulfate Sodium-Induced Murine Colitis by Intracolonic Cyclosporin" *Digest. Dis. Sci.* (1993) 38(9):1722-1734.

Okayasu et al. "A Novel Method in the Induction of Reliable Experimental Acute and Chronic Ulcerative Colitis in Mice" *Gastroenterology* (1990) 98:694-702.

Pan et al. "Advancements in immune tolerance" *Adv Drug Deliv Rev.* (2008) 60(2): 91-105.

Rodriguez et al. "1-Arginine Consumption by Macrophages Modulates the Expression of CD3 ξ Chain in T Lymphoccytes" *J Immunol.* (2003) 171:1232-1239.

Schmielau et al. "Activated Granulocytes and Granulocyte-derived Hydrogen Peroxide Are the Underlying Mechanism of Suppression of T-Cell Function in Advanced Cancer Patients" *Cancer Res.* (2001) 61:4756-4760.

Seiderer et al. "Role of the Novel Th17 Cytokine IL-17F in Inflammatory Bowel Disease (IBD): Upregulated Colonic IL-17F Expression in Active Crohn's Disease and Analysis of the IL17Fp.His161Arg Polymorphism in 1BD" *Inflamm Bowel Dis.* (2008) 14:437-45.

Takeda et al. "Toll-Like Receptors" *Annual Review of Immunology.* (2003) 21:335-376.

Weber et al. "Type II monocytes modulate T cell-mediated central nervous system autoimmune disease" *Nat. Med.* (2007) 13(8): 935-943.

Yang et al. "Regulation of inflammatory responses by IL-17F" *J Exp. Med.* (2008) 205:1063-1075.

International Search Report and Written Opinion dated Sep. 20, 2011 in co-pending Application Serial No. PCT/US2010/061610, 13 pages.

\* cited by examiner

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: synthesized

<400> SEQUENCE: 1
cagctgccta cagtgcccct ag                                22

<210> SEQ ID NO 2
<211> LENGTH: 20
<212> TYPE: DNA
<213> ORGANISM: Artificial Sequence
<220> FEATURE:
<223> OTHER INFORMATION: synthesized

<400> SEQUENCE: 2
catttgccag cagtgggtag                                   20

METHODS OF USING SMALL COMPOUNDS TO ENHANCE MYELOID DERIVED SUPPRESSOR CELL FUNCTION FOR TREATING AUTOIMMUNE DISEASES

RELATED APPLICATIONS

This is a U.S. National Phase application under 35 U.S.C. §371 of International Patent Application No. PCT/US2010/061610, filed Dec. 21, 2010, and claims the benefit of U.S. Provisional Patent Application Ser. No. 61/289,218, filed Dec. 22, 2009, both of which are herein incorporated by reference in their entirety. The International Application published in English on Jul. 21, 2011 as WO 2011/087795 under PCT Article 21(2).

REFERENCE TO SEQUENCE LISTING

Pursuant to 37 C.F.R. 1.821(c), a sequence listing is submitted herewith via EFS-Web as an ASCII compliant text file named "Sequencelisting.TXT" that was created on Jan. 7, 2013, and has a size of 772 bytes. The content of the aforementioned file named "Sequencelisting.TXT" is hereby incorporated by reference in its entirety

FIELD OF THE INVENTION

The present invention is related to methods for enhancing the suppressive function of myeloid derived suppressor cells (MDSCs) for the treatment of autoimmune diseases, graft-versus host disease (GVHD) and organ transplantation rejection using small compounds. In certain aspects, the small compounds are glatiramer acetate (GA) and mitogen activated protein (MAP) kinase inhibitors. In other aspects, these methods include the use of exogenous MDSCs or endogenous MDSCs mobilized using stem cell mobilizers. In yet other aspects, the present invention provides compositions containing MDSCs and small compounds of the invention.

BACKGROUND OF THE INVENTION

Myeloid derived suppressor cells (MDSCs) are increased in numerous pathologic conditions, including infections, inflammatory diseases, graft-versus host disease (GVHD), traumatic stress, and tumor growth. Previous studies have shown that MDSCs can suppress the onset of autoimmune (type 1) diabetes and prevent GVHDs. MDSC-mediated T cell inactivation in vitro has also been reported (Bronte et al., J. Immunol. 2003, 170:270-278; Rodriguez et al., J Immunol. 2003, 171:1232-1239; Bronte et al., Trends Immunol. 2003, 24:302-306; Kusmartsev et al., J. Immunol. 2004, 172: 989-999; Schmielau and Finn, Cancer Res. 2001, 61:4756-4760; Almand et al., J. Immunol. 2001, 166:678; Kusmartsev et al., J. Immunol. 2000, 165:779; Bronte et al., J. Immunol. 1999, 162:5728) MDSCs suppress T-cell responses through production of nitric oxide (NO) (by inducible nitric oxide synthase pathway (iNOS)), arginase, and reactive oxygen species (ROS), and can play an important role in the induction of CD4+CD25+FoxP3+ T regulatory cells through secreting TGF-β and IL-10. [Reviewed in Pan, P. et al. Adv Drug Deliv Rev. 2008 Jan. 14; 60(2): 91-105]. MDSCs exhibit strong immune suppression of T-cell proliferation as well as the ability to induce the development of T regulatory (Treg) cells in tumor-bearing mice. (Pan, P. et al. (2008); Kusmartsev et al. 2000, J. Immunol. 165: 779-785; Huang, et al. 2006, Cancer Res. 66: 1123-1131), however, presently, methods for using MDSCs to induce immune tolerance and to successfully treat inflammatory disease, such as autoimmunity and alloimmune responses are needed.

Alloimmune responses can determine the success or failure of three major transplant events—engraftment of transplanted organs, GVHD and graft-versus-malignancy (GVM) effect. For tissue engraftment, e.g., organ transplantation, immunosuppression of the host immune system permits the transplant to avoid immune rejection. In the case of bone marrow transplantation, immunosuppression of the recipient is needed to allow the graft to gain a foothold. Recipients that do not achieve early donor T cell engraftment are at risk for graft rejection from residual host immune cells (Childs et al., Blood 1999, 94:3234). The direct (contacting antigen presenting cells) or indirect (cytokine induction) expansion of T cells recognizing recipient antigens (alloantigens) leads to tissue damage and GVHD (Ferrara and Deeg, N. Engl. J. Med. 1991, 324:667). GVM is an expansion of transplanted T cells in the bone marrow, but directed against malignant recipient cells, which is a beneficial effect.

Several immunosuppressive compounds exist to combat transplantation rejection, which include, for example, cyclosporine, steroids and methotrexate. However, side effects are associated with each of these drugs, such as kidney toxicity or more rarely neurological problems associated with cyclosporin; weight gain, irritability, and mood swings associated with steroids; and upset stomach, mouth sores, low white blood counts and liver and bone marrow toxicity associated with methotrexate. Attempts to minimize or eliminate GVHD prior to transplantation or transfusion by removing (e.g., with antibodies or by physical separation) or inactivating (e.g., irradiation) donor T cells were unsuccessful because there was an increased risk of rejection, relapse and infectious complications (Horowitz et al., Blood. 1990, 75:555). MDSCs can also inhibit interleukin-2 (IL-2) utilization by NK cells (Brooks et at., 20 Transplantation. 1994, 58:1096) and NK cell activity (Kusmartsev et at., Int. J. Immunopathol. Pharmacol. 1998, 11: 171; Li, H. et al. (2009) "Cancer-Expanded Myeloid-Derived Suppressor Cells Induce Anergy of NK Cells through Membrane-Bound TGF-β1." J. Immunol; 182, 240-249].

Like GVHD, autoimmunity is also driven by inflammatory immune response. The immune system normally avoid generating autoimmune responses by its ability to distinguish between the body's own cells (self) and foreign invaders (non-self). However, sometimes the immune system's recognition apparatus becomes misdirected and the body begins to mount an immune response directed against its own cells and organs. These misguided T cells and autoantibodies cause what are referred to as autoimmune diseases, which are a varied group of more than 80 serious, chronic illnesses that affect many human organ systems and tissues. For example, T cells that attack pancreas cells contribute to diabetes, while autoantibodies are common in people with rheumatoid arthritis. In another example, patients with systemic lupus erythematosus have antibodies to many types of their own cells and cell components. The treatment of autoimmune diseases depends on the type of disease, how severe it is and the symptoms. Therefore, the treatment may vary from relieving symptoms to preserving organ function (e.g., insulin injections to regulate blood sugar in diabetics) to targeting disease mechanisms (e.g., immunosuppressive drugs or immunomodulators).

Significant progress in understanding the pathogenesis of a family of autoimmune diseases known as inflammatory bowel disease (IBD) has been made in the past few years. Murine models, which mimic many features of IBD, have shown that IBD results from an imbalance between effector and regulatory T cell. Mucosal inflammation has been suggested to cause an excessive effector function against mucosal antigens, which in combination with the lack of regulatory response to these antigens, leads to the development of autoimmune IBD.

To date there are no methods for treating autoimmune diseases or alloimmune reactions that do not have undesirable side-effect profiles. Therefore, there remains a need for a method to treat or prevent autoimmune disease or alloimmune reactions while preserving a GVM effect, and at the same time does not cause severe side effects. The instant invention fills such a need and provides other related advantages.

SUMMARY OF THE INVENTION

As stated above, there remains a need in the art for effective and safe methods for the treatment of autoimmune diseases and prevention of alloimmune responses. The present invention fills such needs and provides other related advantages.

In certain aspects, the present invention provides a method for suppressing a pro-inflammatory immune response in a mammal, which comprises administering to a mammal in need of such treatment an effective amount for suppressing the pro-inflammatory immune response of a myeloid derived suppressor cell (MDSC) and glatiramer acetate (GA) or a small compound inhibitor of c-Jun N-terminal kinase (JNK). In another aspect, the present invention provides a method for suppressing a pro-inflammatory immune response in a mammal, which comprises administering to a mammal in need of such treatment an effective amount for suppressing the pro-inflammatory immune response of a MDSC, GA and a small compound inhibitor of JNK.

In one aspect, the present invention provides a method for treating an autoimmune disease, which comprises administering to a mammal in need of such treatment an effective amount for treating the autoimmune disease of a composition comprising a MDSC and GA or a small compound inhibitor of JNK. In another aspect, the present invention provides a method for treating an autoimmune disease, which comprises administering to a mammal in need of such treatment an effective amount for treating the autoimmune disease of a composition comprising a MDC, GA and a small compound inhibitor of JNK.

In one embodiment, the present invention provides a method for suppressing a pro-inflammatory immune response in a mammal, which comprises administering to a mammal in need of such treatment an effective amount for suppressing the pro-inflammatory immune response of at least one stem cell mobilizing agent, and GA or a small compound inhibitor of JNK. In some embodiments, the present invention provides a method for suppressing a pro-inflammatory immune response in a mammal, which comprises administering to a mammal in need of such treatment an effective amount for suppressing the pro-inflammatory immune response of at least one stem cell mobilizing agent, GA and a small compound inhibitor of JNK.

In certain embodiments, the invention provides a method for treating an autoimmune disease, which comprises administering to a mammal in need of such treatment an effective amount for treating the autoimmune disease of at least one stem cell mobilizing agent, and GA or a small compound inhibitor of JNK. In another embodiment, the invention provides a method for treating an autoimmune disease, which comprises administering to a mammal in need of such treatment an effective amount for treating the autoimmune disease of at least one stem cell mobilizing agent, GA and a small compound inhibitor of JNK.

In one embodiment, the invention provides a method for suppressing a pro-inflammatory immune response in a mammal, which comprises administering to a mammal in need of such treatment an effective amount for suppressing the pro-inflammatory immune response of a MDSC and GA or a small compound MAP kinase inhibitor. In other embodiments, the invention provides a method for suppressing a pro-inflammatory immune response in a mammal, which comprises administering to a mammal in need of such treatment an effective amount for suppressing the pro-inflammatory immune response of a MDSC, GA and a small compound MAP kinase inhibitor.

In a certain aspect, the invention provides a method for treating an autoimmune disease, which comprises administering to a mammal in need of such treatment an effective amount for treating the autoimmune disease of a composition comprising a MDSC and GA or a small compound MAP kinase inhibitor. In other aspects, the invention provides a method for treating an autoimmune disease, which comprises administering to a mammal in need of such treatment an effective amount for treating the autoimmune disease of a composition comprising a MDSC, GA and a small compound MAP kinase inhibitor.

In another aspect, the invention provides a method for suppressing a pro-inflammatory immune response in a mammal, which comprises administering to a mammal in need of such treatment an effective amount for suppressing the pro-inflammatory immune response of at least one stem cell mobilizing agent, and GA or a small compound MAP kinase inhibitor. In yet another aspect, the invention provides a method for suppressing a pro-inflammatory immune response in a mammal, which comprises administering to a mammal in need of such treatment an effective amount for suppressing the pro-inflammatory immune response of at least one stem cell mobilizing agent, GA and a small compound MAP kinase inhibitor.

In certain embodiments, the present invention provides a method for treating an autoimmune disease, which comprises administering to a mammal in need of such treatment an effective amount for treating the autoimmune disease of at least one stem cell mobilizing agent, and GA or a small compound MAP kinase inhibitor. In certain other embodiments, the present invention provides a method for treating an autoimmune disease, which comprises administering to a mammal in need of such treatment an effective amount for treating the autoimmune disease of at least one stem cell mobilizing agent, GA and a small compound MAP kinase inhibitor.

In certain aspects, the present invention provides a pharmaceutical composition, which comprises: (a) an MDSC; (b) GA or a small compound inhibitor of JNK; and (c) a pharmaceutically acceptable carrier or diluent. In other embodiments, the present invention provides a pharmaceutical composition, which comprises: (a) an MDSC; (b) GA; (c) a small compound inhibitor of JNK; and (d) a pharmaceutically acceptable carrier or diluent.

In one embodiment, the present invention provides a pharmaceutical composition, which comprises: (a) an MDSC; (b) GA or a small compound MAP kinase inhibitor; and (c) a pharmaceutically acceptable carrier or diluent. In yet another embodiment, the present invention provides a pharmaceutical composition, which comprises: (a) an MDSC; (b) GA; (c) a small compound MAP kinase inhibitor; and (d) a pharmaceutically acceptable carrier or diluent.

In yet other aspects, the present invention provides a pharmaceutical composition, which comprises: (a) at least one stem cell mobilizing agent; (b) GA or a small compound MAP kinase inhibitor; and (c) a pharmaceutically acceptable carrier or diluent. In still other aspects, the present invention provides a pharmaceutical composition, which comprises: (a) at least one stem cell mobilizing agent; (b) GA; (c) a small compound MAP kinase inhibitor; and (d) a pharmaceutically acceptable carrier or diluent.

In certain of the above embodiments of the invention the pro-inflammatory immune response can be suppressed by generating a T regulatory cell response. In certain of the above embodiments, the pro-inflammatory immune response comprises a T cell response, and the T cell response is suppressed by MDSCs through production of nitric oxide, arginase, and/or reactive oxygen species (ROS). In certain embodiments of invention, the pro-inflammatory immune response is an alloimmune response.

In any of the aspects of the invention, the mammal may be a human.

In certain of the above embodiments of the present invention, the autoimmune disease is selected from the group consisting of coeliac disease, type I diabetes, multiple sclerosis, thyroiditis, Grave's disease, systemic lupus erythematosus, scleroderma, psoriasis, arthritis, rheumatoid arthritis, alopecia greata, ankylosing spondylitis, Churg-Strauss Syndrome, autoimmune hemolytic anemia, autoimmune hepatitis, Behcet's disease, Crohn's disease, dermatomyositis, glomerulonephritis, Guillain-Barre syndrome, IBD, lupus nephritis, myasthenia gravis, myocarditis, pemphigus/pemphigoid, pernicious anemia, polyarteritis nodosa, polymyositis, primary biliary cirrhosis, rheumatic fever, sarcoidosis, Sjogren's syndrome, ulcerative colitis, uveitis, vitiligo, and Wegener's granulomatosis.

In certain aspects of the invention, a method for treating an autoimmune disease in a subject is provided, which comprises administering to a subject in need of such treatment any of the pharmaceutical compositions of the invention in an effective amount for treating an autoimmune disease. In other aspects, the invention provides a method for suppressing a pro-inflammatory immune response in a subject, which comprises administering to a subject in need of such treatment any one of the pharmaceutical compositions of the invention in an effective amount for suppressing a pro-inflammatory immune response.

In certain of the above embodiments, the at least one stem cell mobilizing agent is selected from the group consisting of G-CSF, AMD 3100, CTCE-9908, FTY720, Flt3 ligand, stem cell factor (SCF), S100A9, GM-CSF and M-CSF.

In certain above aspects of the invention, the small compound inhibitor of JNK is SP600125. In other aspects, the small compound MAP kinase inhibitor is selected from the group consisting of SP600125, AM111, JNK930, XG102, CEP-1347, SB203580, PD98059, ARRY-797, ARRY-614, BMS582949, CNI1493, 610677, 856553, and GSK681323.

These and other aspects of the present invention will be apparent to those of ordinary skill in the art in light of the present specification, claims and drawings.

DETAILED DESCRIPTION OF THE INVENTION

Figure 1A:
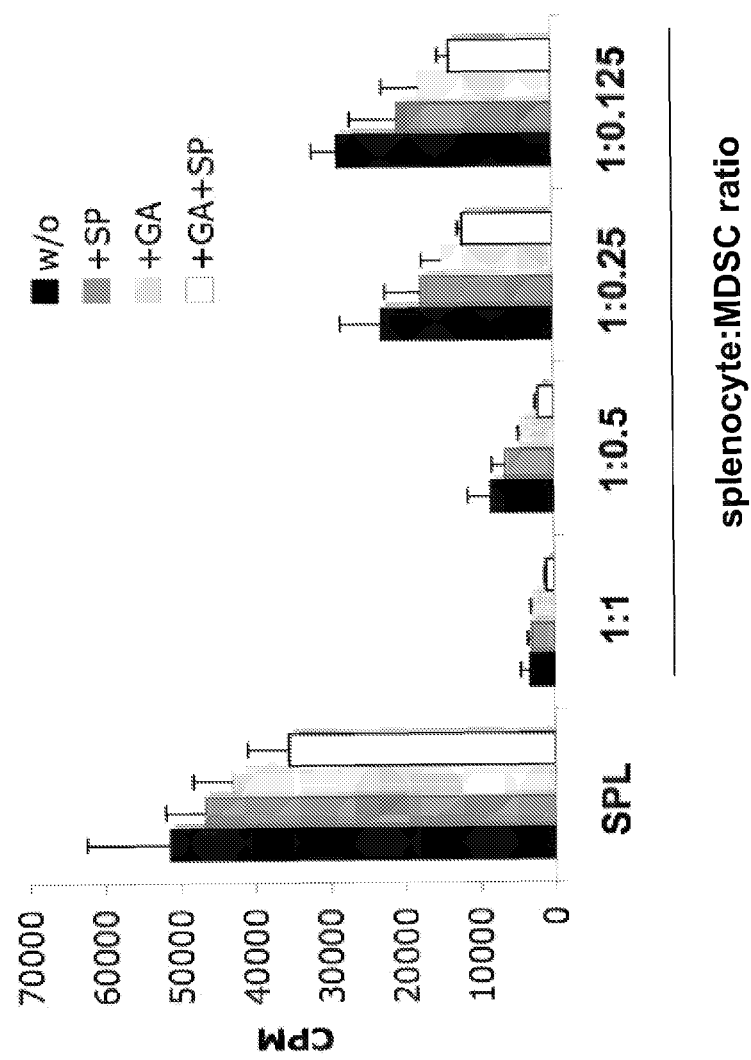
FIG. 1A: A bar graph showing that the small compounds GA and SP600125 synergistically enhance the suppressive activity of MDSCs in vitro. The ratios on the X-axis are splenocyte:MDSC. "SPL" indicates untreated naïve splenocytes (i.e. without MDSC).

The present invention provides methods of treating an autoimmune disease or alloimmune response in an individual.

The present invention is based in part on the discovery that administration of myeloid derived suppressor cells (MDSCs) in combination with GA or a MAP kinase inhibitor, or in combination with GA and a MAP kinase inhibitor, is surprisingly effective for the treatment of inflammatory bowel disease (IBD), an autoimmune disease. Moreover, it is presently discovered that GA and the small compound c-Jun N-terminal kinase (JNK), SP600125, have a surprising, synergistic effect in combination.

In certain embodiments, methods for suppressing an immune response in a mammal are provided. The present invention is further directed to methods for enhancing the suppressive functions of MDSCs for the treatment of an autoimmune disease or alloimmune response in an individual using small compounds. In certain aspects, MDSCs are administered with either GA or a small compound MAP kinase inhibitor alone, or with both, to a patient with an autoimmune disease or alloimmune response. In a specific embodiment, MDSCs are administered to a subject or patient with GA and the small compound JNK inhibitor, SP600125.

In one aspect, MDSCs in combination with small compounds are administered intravenously. In yet another aspect, endogenous MDSCs are mobilized to an inflammatory site (such as a site of disease), using stem cell mobilizers, such as, e.g., G-CSF, AMD 3100, CTCE-9908, FTY720, GM-CSF, M-CSF, stem cell factor (SCF), S100A9 and/or Flt3 ligand, and then small compounds such as GA and/or SP600125 are administered separately from the stem cell mobilizers, by, e.g., intravenous, oral, or subcutaneous administration.

The term "subject" or "individual" as used herein refers to an animal having an immune system, preferably a mammal (e.g., rodent, such as mouse). In particular, the term refers to humans.

As used herein, the term "about" or "approximately" usually means within an acceptable error range for the type of value and method of measurement. For example, it can mean within 20%, more preferably within 10%, and most preferably still within 5% of a given value or range. Alternatively, especially in biological systems, the term "about" means within about a log (i.e., an order of magnitude) preferably within a factor of two of a given value.

As used herein, the term "pro-inflammatory immune response" includes both adaptive (e.g., T cell- and B cell-mediated) and innate (e.g., natural killer (NK) cell, macrophage, dendritic cells-mediated) immune responses. The term "suppressing a pro-inflammatory immune response" means that the pro-inflammatory immune response, as measured the innate or adaptive immune response, is either significantly reduced or completely abrogated.

The phrase "T cell response" means an immunological response involving T cells, such as Th1, Th2 and Th17 cells and/or CD8 T cells. The phrase includes all aspects of the T cell response, including generation of an antigen-specific effector T cells and/or memory T cells.

The term "Treg cell" refers to a T cell that can inhibit, reduce or suppress an immune response, including a T cell response, and/or maintain or induce immune tolerance.

The term "inducing Treg cells" means activating Treg cells to inhibit or reduce the immune response, such as a T-cell mediated response or pro-inflammatory response. For example, one method of induction is through the use of the MDSCs, small compounds and/or stem cell mobilizer-containing compositions of the present invention.

The phrase "T cell tolerance" refers to the anergy (non-responsiveness) of T cells when presented with an antigen. T cell tolerance prevents a T cell response even in the presence of an antigen that existing memory T cells recognize.

An "autoimmune disease" or "autoimmune response" is a response in which the immune system of an individual initiates and may propagate a pro-inflammatory immune response against its own tissues or cells. An "alloimmune response" is one in which the immune system of an individual initiates and may propagate a a pro-inflammatory immune response against the tissues, cells, or molecules of another, as, for example, in a transplant or transfusion.

As used herein, the term "transplant rejection" means that a transplant of tissue or cells is not tolerated by a host individual. The transplant is not tolerated in that it is attacked by the host's own immune system or is otherwise not supported by the host. The transplant may be an allotransplant, a transplant of tissue or cells from another individual of the same species, or an autotransplant, a transplant of the host's own tissue or cells. Transplant rejection encompasses the rejection of fluids through transfusion.

As used herein, the term "cytokine" is a generic term for a group of proteins released by one cell population which act on another cell population as intercellular mediators. Examples of such cytokines are lymphokines, monokines, and traditional polypeptide hormones. Included among the cytokines are interferons (IFN, notably IFN-γ), interleukins (IL, notably IL-1, IL-2, IL-4, IL-10, IL-12), colony stimulating factors (CSF), macrophage colony stimulating factor (M-CSF), granulocyte macrophage colony stimulating factor (GM-CSF), granulocyte colony-stimulating factor (G-CSF), thrombopoietin (TPO), erythropoietin (EPO), leukemia inhibitory factor (LIF), kit-ligand, Flt3 ligand, growth hormones (GH), insulin-like growth factors (IGF), parathyroid hormone, thyroxine, insulin, relaxin, follicle stimulating hormone (FSH), thyroid stimulating hormone (TSH), leutinizing hormone (LH), hematopoietic growth factor, hepatic growth factor, fibroblast growth factors (FGF), prolactin, placental lactogen, TNF, mullerian-inhibiting substance, mouse gonadotropin-associated peptide, inhibin, activin, vascular endothelial growth factor (VEGF), integrin, nerve growth factors (NGF), stem cell factor (SCF), platelet growth factor, transforming growth factors (TGF), osteoinductive factors, etc.

"Treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving the disease, i.e., causing regression of the state, disorder or condition or at least one of its clinical or subclinical symptoms.

The benefit to an individual to be treated is either statistically significant or at least perceptible to the patient or to the physician.

Myeloid Derived Suppressor Cells

In certain embodiments of the present invention, methods for treating autoimmune diseases or alloimmune responses using MDSCs are provided. In other embodiments, the methods of the present invention are useful for treating transplant rejection.

The term "MDSC" refers to a cell with an immunosuppressive function that is of hematopoietic lineage and expresses Gr-1 and CD115. [See, Li et al., Cancer Res. 2004, 64:1130-1139; Pan, P. et al. (2008)] MDSCs, which are also known as myeloid suppressor cells (MSCs), are also CD11b+ and Ly6C+ and may also express F4/80. CD115 (macrophage colony-stimulating factor receptor) is an early marker of myeloid progenitor cell and is also expressed by normal monocytes from naive mice. They are composed of precursors of macrophages, granulocytes, and dendritic cells, and of earlier stages of myeloid cells. MDSCs can be induced to differentiate into mature granulocytes, macrophages, and dendritic cells upon culture in the presence of the appropriate cytokine cocktail [Apolloni et al., 2000, J. Immunol. 165: 6723-6730; Bronte et al., 2000 Blood 96: 3838-46; Kusmartsev et al., 2003, Cancer Res. 63:4441-4449; Li et al., 2004, Cancer Res. 64:1130-1139]. MDSCs can also spontaneously differentiate in culture and express lineage markers such as CD11c, MHC molecules (class I and class II), F4/80 and costimulatory molecules (e.g., CD80 and CD86).

In certain embodiments of the invention, small molecules of the invention are used to sustain and enhance the suppressive functions of MDSCs by preventing the MDSCs to undergo maturation and terminal differentiation. The immature stage of MDSCs is characterized by low cell surface expression of MHC class II, co-stimulatory molecules, e.g., CD80, CD86, CD40, low CD11c and F4/80 Immature MDSCs are further characterized by a large nucleus to cytoplasm ratio and an immunosuppressive activity.

In some embodiments of the invention, MDSCs are autologously-derived cells. For example, MDSCs may be isolated from normal adult bone marrow or from sites of normal hematopoiesis, such as the spleen. MDSCs are scant in the periphery and are present in a low number in the bone marrow of healthy individuals. However, they are accumulated in the periphery when intense hematopoiesis occurs. Upon distress due to graft-versus-host disease (GVHD), cyclophosphamide injection, or g-irradiation, for example, MDSCs may be found in the adult spleen. Thus, in certain embodiments, MDSCs may be isolated from the adult spleen. MDSCs may also be isolated from the bone marrow and spleens of tumor-bearing or newborn mice. In a preferred embodiment, MDSCs are isolated in vivo by mobilizing MDSCs from hematopoietic stem cells (HSCs) or bone marrow suing stem cell mobilizers such as G-CSF (R&D Systems®, Minneapolis, Minn.), AMD 3100 (Tocris Bioscience, Ellisville, Mo.) [see, Larochelle, A. et al. (2006) Blood, Vol. 107 (9):3772-3778], CTCE-9908 (Chemokine Therapeutics Corp.), FTY720 (Cayman Chemical, Ann Arbor, Mich.) [see, Kimura, T. et al. (2004) Blood; June 15; 103(12):4478-86], S100A9 [see, Cheng et al (2008) J. Exper. Med. Vol. 205, No. 10, 2235-2249], GM-CSF, M-CSF and SCF and/or Flt3 ligand (R&D Systems®). Any suitable stem cell mobilizer or combination of mobilizers is contemplated for use in the present invention. MDSCs may be induced endogenously and/or be collected from the blood e.g., by apheresis, following treatment of a subject or patient with the stem cell mobilizer(s).

In certain embodiments, MDSCs can be derived, for example, in vitro from a patient's HSCs, from MHC matching ES cells, induced pluripotent stem (iPS) cells [see, Baker, Monya (2007). "Adult cells reprogrammed to pluripotency, without tumors". *Nature Reports Stem Cells*. published online]. Methods for expanding MDSCs in vitro are described in detail in U.S. Publication No. 2008/0305079 by Chen. Specifically, isolated hematopoietic stem cells (HSCs) can be stimulated to differentiate into Gr-1+/CD11b+, Gr-1+/ CD11b.+/CD115+, Gr-1+/CD11b+/F4/80+, or Gr-1+/ CD11b+/CD115+/F4/80+ MDSCs by culturing in the presence of stem-cell factor (SCF) or SCF with tumor factors, which can increase the MDSC population. The culture conditions for mouse and human HSCs are described in detail in U.S. Publication No. 2008/0305079 by Chen.

In further embodiments, other cytokines may be used, e.g., VEGF, GM-CSF, M-CSF, SCF, S100A9, TPO, IL-6, IL-1, PGE-2 or G-CSF (all commercially available, e.g. from R&D Systems®) to stimulate MDSC differentiation from HSCs in vitro. Any one of the cytokines may be used alone or in combination with other cytokines. In still another embodiment, tumor-conditioned media may be used with or without SCF to stimulate HSCs to differentiate into MDSCs.

In other embodiments, MDSCs are allogeneic cells, such as MDSCs obtained or isolated from a donor or cell line. MDSC cell lines and exemplary methods for their generation are well known in the art and are described in the literature. [See, e.g., Apolloni et al. (2000) "Immortalized myeloid suppressor cells trigger apoptosis in antigen-activated T lymphocytes." *J. Immunol.* 165:6723; Mazzoni et al. (2002) "Myeloid Suppressor Lines Inhibit T Cell Responses by an NO-Dependent Mechanism;" *J. Immunol.* 168:689-695.]

Small Compounds

In certain aspects of the invention, the small compound glatiramer acetate (GA) (Copolymer 1/Copaxone) is used to modify MDSC function. In another aspect, a small compound MAP kinase inhibitor is used to modify MDSC function. In yet another aspect, GA and a small compound MAP kinase inhibitor, such as, e.g., a c-Jun N-terminal kinase (JNK) small compound inhibitor, have a surprising synergistic effect on the modulation of MDSC function for the treatment or prevention of alloimmune response and pro-inflammatory immune responses.

Signal regulation by small compounds (e.g., small molecule inhibitors) can control cell differentiation and function. The term "small compound" as used herein refers to compounds, chemicals, small molecules, small molecule inhibitors, or other factors that are useful for modulating MDSC function. Small molecule inhibitors have been used as immunosuppressive and anti-inflammatory drugs. GA (Copolymer 1/Copaxone) is an FDA approved drug for the treatment of multiple sclerosis, a T cell-mediated autoimmune disease. SP600125 is a small compound inhibitor of JNK, which is a downstream molecule of a number of signaling pathways that regulate both innate and adaptive immunity. The present invention is related to the discovery that these small compounds can regulate the suppressive functions of MDSCs to facilitate the establishment of immune tolerance.

Significantly, GA alone has not been effective for treating autoimmune diseases. Specifically, GA is known to be only partially effective for treating the autoimmune disease multiple sclerosis [Johnson et al. (1995) *Neurology* 45: 1268-1276]. Moreover, clinical studies using GA for the treatment of IBD were discontinued, because GA failed to treat IBD. The present invention is based on the discovery that administration of GA in combination with MDSCs, or with MDSCs and a MAP kinase inhibitor (e.g., SP600125), is surprisingly effective for the treatment of the autoimmune disease, IBD. It is presently discovered that GA and SP600125 have a synergistic effect in combination.

COPAXONE™ is the brand name for GA (formerly known as copolymer-1). GA, the active ingredient of COPAXONE™, is a random polymer consisting of the acetate salts of synthetic polypeptides, containing four naturally occurring amino acids: L-glutamic acid, L-alanine, L-tyrosine, and L-lysine with an average molar fraction of 0.141, 0.427, 0.095, and 0.338, respectively [CAS number 147245-92-9]. The average molecular weight of GA is 4,700 11,000 daltons. Chemically, glatiramer acetate is designated L-glutamic acid polymer with L-alanine, L-lysine and L-tyrosine, acetate (salt). GA is a random polymer composed of tyrosine, glutamic acid, alanine and lysine, that has been used for the treatment of multiple sclerosis, a T cell-mediated autoimmune disease. GA may be obtained from Teva Pharmaceutical Industries (Petach Tikva, Israel).

In the present invention, variants, modified forms and/or derivatives of GA are also contemplated for use in the present invention. One of skill in the art can readily substitute structurally-related amino acids for GA without deviating from the spirit of the invention. The present invention includes polypeptides and peptides which contain amino acids that are structurally related to tyrosine, glutamic acid, alanine or lysine and possess the ability to stimulate polyclonal antibody production upon introduction. Such substitutions retain substantially equivalent biological activity in their ability to suppress autoimmune diseases such as IBD, and alloimmune responses, such as GVHD and organ transplantation rejection. These substitutions are structurally-related amino acid substitutions, including those amino acids which have about the same charge, hydrophobicity and size as tyrosine, glutamic acid, alanine or lysine. For example lysine is structurally-related to arginine and histidine; glutamic acid is structurally-related to aspartic acid; tyrosine is structurally-related to serine, threonine, phenylalanine and tryptophan; and alanine is structurally-related to valine, leucine and isoleucine. These and other conservative substitutions, such as structurally-related synthetic amino acids, are contemplated by the present invention. Any one or more of the amino acids in GA may be substituted with 1- or d-amino acids. As is known by one of skill in the art, 1-amino acids occur in most natural proteins. However, d-amino acids are commercially available and can be substituted for some or all of the amino acids used to make GA. Thus, in some embodiments, the present invention contemplates GA formed from mixtures of d- and 1-amino acids.

While not intended to be bound by any specific theory, GA is thought to cause disruption of the T cell-antigen reactivity. Specifically, it has been previously described that GA binds promiscuously with high affinity to various class II major histocompatibility (MHC) molecules of murine and human origin and can displace antigens from the MHC antigen-binding groove. This competition for MHC binding can hinder the presentation of other antigens and consequently lead to inhibition of various effector functions. GA has also been shown to be a potent inducer of Th2/Th3 (Treg) cells that secrete high amounts of IL-10 and TGF-β. [See, Aharoni et al. *Immunology Letter* 112 (2007) 110-119; Aharoni et al. *Proc Natl Acad Sci* USA (1997); 94:10821-6].

Within certain embodiments, other small compounds can be used in addition to or in place of GA. For example, myelin basic protein, glutamic acid, lysine, alanine and tyrosine can also be used like GA as an immune system decoy, leading to enhanced suppression of T cell responses. Within other embodiments, the agonistic cannabinoid receptor 1 (CB1) and CB2 can be used to enhance MDSC-mediated suppression and migration from the bone marrow.

Recent reports indicate that GA treatment may exert immunomodulatory activity on antigen presenting cell (APCs) and may promote the development of monocytes that secrete an anti-inflammatory type II cytokine in mice. [See, Weber et al. (2007) *Nat. Med.* 13(8): 935-943.] However, whether these small compounds can regulate the suppressive functions of MDSCs to facilitate the establishment and maintenance of immune tolerance and the underlying mechanisms of action was not known. The present invention is related to the discovery that GA alone can in fact regulate and prolong the suppressive activity of MDSCs. Moreover, the invention is related to the present discovery that the action of GA is synergistically enhanced by combination with the small compound MAP kinase inhibitor SP600125.

SP600125 (1,9-Pyrazoloanthrone, Anthrapyrazolone) (Sigma-Aldrich) is a small compound inhibitor of the MAP kinase, JNK (c-Jun N-terminal kinase), which is a downstream molecule of a number of signaling pathways that regulate both innate and adaptive immunity. [Bennett et al., 2001, Proc Natl Acad Sci USA. 98:13681-13686.] JNK is involved for example, in the MyD88-dependent TLR signaling pathways, which are involved in the generation of immune responses. Non-limiting examples of other JNK inhibitors contemplated for use in the present invention include, for example, AM111 from Auris Medical AG (Basel, Switzerland), JNK930 from Celgene Corporation (Summit, N.J.), XG102 from RibOvax Biotechnologies S.A. (Geneva, Switzerland), and CEP-1347 from Cephalon Inc. (Frazer, Pa.).

AM111 is a cell permeable peptide otoprotectant which selectively blocks JNK MAPK-mediated apoptosis of stress injured hair cells and neurons in the cochlea. AM111 is being developed for the treatment of acute sensorineural hearing loss from acute acoustic trauma. JNK930 is a JNK inhibitor, which is being developed for the treatment of fibrotic diseases. XG-102, a neuroprotectant, is a TAT-coupled dextrogyre peptide which selectively inhibits JNK. XG-102 is being developed for the treatment of severe diseases of the eye such as diabetic retinopathy, AMD (age-related macular degeneration), and uveitis.

Any small compound MAP kinase inhibitor that has a similar biological effect as SP600125, as described in the present Examples, is contemplated for use in the present invention. Like SP600125, other MAP kinase inhibitors can also retard MDSC differentiation, and therefore enhance MDSC suppressive function and Treg inducing capability. In some embodiments, small compound inhibitors such as, but not limited to JNK, Erk and p38α,β (p38) are contemplated for use the present invention. Examples of MAP kinase inhibitors include but are not limited to ARRY-797, ARRY-614 and BMS582949 (Array BioPharma Inc., Boulder, Colo.), CNI1493 (Cytokine PharmaSciences Inc., King of Prussia, Pa.), 610677, 856553, GSK681323 (GlaxoSmithKline plc, Brentford, Middlesex, United Kingdom), PD98059 and SB203580 (Sigma-Aldrich).

For example, ARRY-797 is a selective, orally-active inhibitor of p38. ARRY-797 is being developed for the treatment of inflammatory pain. ARRY-614 is a potent, orally-active inhibitor of p38, Ab1, Tie2 and VEGFR2. BMS-582949 is an oral p38 kinase inhibitor whose inhibition of p38 kinase down-regulates intracellular activation of enzymes. These enzymes normally promote the production of a broad array of inflammatory cytokines including TNF and IL-1. BMS-582949 is being developed for the treatment of atherosclerosis. CNI-1493 contains semapimod, a synthetic guanylhydrazone, is a cytokine inhibitor and MAP kinase blocker. It inhibits signal transduction pathways by preventing phosphorylation of p38 MAP kinase and JNK, production of the proinflammatory cytokines TNF-α, IL-1, IL-6, MIP-1α, MIP-1β and production of nitric oxide. CNI-1493 is being developed as an intravenous formulation for the treatment of moderate to severe Crohn's disease. 610677 is a p38 kinase inhibitor which exerts pulmonary anti-inflammatory activity. 610677 is being developed for the treatment of chronic obstructive pulmonary disease. 856553 is a p38 kinase inhibitor being developed for the treatment of atherosclerosis. Its active ingredient is iosmapimod. GSK681323 is a p38α kinase inhibitor and is being developed for the treatment of atherosclerosis and chronic obstructive pulmonary disease (COPD) and for the treatment of neuropathic pain.

Another non-limiting example is SB203580 (4-(4-Fluorophenyl)-2-(4-methylsulfinylphenyl)-5-(4-pyridyl)-1H-imidazole), which is a pyridinyl imidazole that suppresses the activation of MAPKAP kinase-2 and inhibits the phosphorylation of heat shock protein (HSP) 27 in response to IL-1, cellular stresses and bacterial endotoxin in vivo. It does not inhibit JNK or p42 MAP kinase and therefore, is useful for studying the physiological roles and targets of p38 MAPK and MAPKAP kinase-2. It has been shown to induce the activation of the serine/threonine kinase Raf-1 and has been reported to inhibit cytokine production. PD98059 (2-(2-Amino-3-methoxyphenyl)-4H-1-benzopyran-4-one) is a specific inhibitor of the activation of mitogen-activated protein kinase kinase (MAPKK).

Mobilization of MDSCs Using Stem Cell Mobilizers

As described in the present Examples, the potential of exogenous MDSCs, or endogenous MDSCs mobilized from bone marrow using stem cell mobilizers, in conjunction with GA and SP600125 was evaluated as a novel therapeutic modality for the treatment of the autoimmune disease, IBD. Stem cell mobilizers are agents which are useful for inducing the increased circulation of CD34+ hematopoietic stem cells from the bone marrow. These stem cells are present in adult vertebrates, including in mammals, and are multi-potential stem cells. The term "hematopoietic stem cell (HSC)" refers to a cell that can give rise to all blood and lymphoid cell types including, for example, red blood cells, platelets, white blood cells, MDSCs, B cells, and T cells. HSCs can also propagate themselves, i.e., give rise to other HSCs, and may give rise to non-hematological cell types. HSC also have a long term reconstitution ability. HSCs are large cells that express Sca-1 and c-kit, have a high nucleus-to-cytoplasm ratio, and may express CD34. In humans, stem cell mobilizers such as G-CSF, AMD 3100, CTCE-9908, FTY720, Flt3 ligand, SCF, S100A9, GM-CSF and M-CSF can be used to mobilize endogenous HSCs to become MDSCs. In some embodiments of the invention, such mobilizers may be used alone or in combination of two or more such stem cell mobilizers. [See, Liles, W. C. et al. (2003) "Mobilization of hematopoietic progenitor cells in healthy volunteers by AMD3100, a CXCR4 antagonist," Blood; 102(8):2728-2730; Flomenberg, N. et al. "The use of AMD3100 plus G-CSF for autologous hematopoietic progenitor cell mobilization is superior to G-CSF alone," (2005) Blood; 106(5):1867-1874.]

Regulatory T (Treg) Cells

Regulatory T (Treg) cells are a specialized subpopulation of T cells that act to suppress activation of the immune system and thereby maintain immune system homeostasis and tolerance to self-antigens. Treg cells are CD4+ T cells that are identified by their expression of CD25 and Foxp3. The expression of Foxp3 may be identified by intracellular staining of the Foxp3 protein, or by RT-PCR to quantify expression of the Foxp3 gene. CD4+CD25+Foxp3+ Treg cells are an important subclass of Treg cells that can attenuate autoreactive T cell responses, which drive autoimmunity. They may also be important for regulating alloimmune responses.

Autoimmunity

In certain aspects of the invention, MDSCs are useful for suppressing immune responses, such as an autoimmune or alloimmune response. The immunosuppressive activity of a cell may be determined by measuring its ability to suppress T-cell proliferation, induce Treg cells, suppress a Th17- or NK cell-mediated response, increase production of suppressive (anti-inflammatory cytokines) such as e.g., TFG-β and IL-10, and/or to decrease secretion of pro-inflammatory cytokines such as e.g. IL-23, IFN-γ and IL-17. Other well-known methods may also be used for measuring the immunosuppressive activity of MDSCs.

Autoimmunity is the failure of an organism to recognize its own constituent parts as self, which allows the generation of an immune response against its own cells and tissues. Any disease that results from such an aberrant immune response is termed an autoimmune disease. The methods of the present invention are useful for treating autoimmune diseases. Prominent examples of autoimmune diseases that may benefit from the methods of the invention include but are not limited to coeliac disease, type I diabetes, multiple sclerosis, thyroiditis, Grave's disease, systemic lupus erythematosus, scleroderma, psoriasis, arthritis, rheumatoid arthritis, alopecia greata, ankylosing spondylitis, Churg-Strauss Syndrome, autoimmune hemolytic anemia, autoimmune hepatitis, Behcet's disease, Crohn's disease, dermatomyositis, glomerulonephritis, Guillain-Barre syndrome, IBD, lupus nephritis, myasthenia gravis, myocarditis, pemphigus/pemphigoid, pernicious anemia, polyarteritis nodosa, polymyositis, primary biliary cirrhosis, rheumatic fever, sarcoidosis, Sjogren's syndrome, ulcerative colitis, uveitis, vitiligo, and Wegener's granulomatosis, and other T cell-mediated immune diseases.

Inflammatory bowel diseases (IBDs) are immunological disorders characterized by dysregulated immune reactivity in the gut and imbalance between pro-inflammatory and anti-inflammatory responses. The major types of IBD are Crohn's disease and ulcerative colitis. The macrophage is considered part of the destructive force in regulating the onset of IBD, as a result of its involvement in producing pro-inflammatory cytokines and chemokines (Autschbach, F., Giese, T., et al., 2002, Virchows Arch. 441:500-13). Moreover, IBDs are thought to be primarily mediated by IL-17. Thus, Th17 cells are thought to play a significant role in IBDs. Studies in the dextran sulfate sodium (DSS)-induced colitis, showed that IL-17F deficiency results in reduced colitis, whereas IL-17A-null mice develop more severe disease [Yang et al., 2008, The J. Exp. Med. 205:1063-1075] [Seiderer J., et al., 2008, Inflamm Bowel Dis. 14:437-45] Therefore, the methods and compositions of the present invention are particularly useful for treating IBDs.

In certain embodiments, the methods of the present invention are also useful for the treatment of leukemia patients with an autoimmune disease. For example, ulcerative colitis, Crohn's disease and other IBDs have been reported to be associated with myelodysplastic syndromes (MDS) or acute myeloid leukemia (AML) [Dombret H, Marolleau J P. Nouv Rev Fr Hematol. 1995; 37(3):193-6; Caspri et al., Leukemia & Lymphoma, 1995, Vol. 17, No. 3-4, Pages 255-262]. Thus, in some embodiments, stem cell mobilizers (such as but not limited to G-CSF and/or AMD310) are administered to a leukemia patient with an autoimmune disease, which increase the frequency of circulating MDSCs in the blood. The blood is subjected to apheresis to collect leukocytes, and then MDSCs are isolated by cell sorting. In other embodiments, MDSCs may be obtained by isolating HSCs from the leukemia patient's bone marrow and differentiating the HSCs into MDSCs according to the methods described supra. The leukemia patient's MDSCs are then irradiated and administered back to the patient after the patient has undergone treatment for leukemia (e.g., whole body irradiation or chemotherapy and bone marrow or stem cell transfer) in a composition of the present invention.

Thus, in certain embodiments of the invention, MDSCs are irradiated prior to administration to a patient. In a specific embodiment of the invention, the invention provides a method for treating a leukemia patient with AML, which comprises administering to a patient in need of such treatment an effective amount for treating AML of irradiated MDSCs, GA and/or a small compound MAP kinase inhibitor, such as, e.g., a JNK inhibitor such as SP 600125.

Alloimmune Responses

According to the methods of the present invention, MDSC-mediated immunosuppression in conjunction with the small compounds of the invention (e.g., GA and SP600125), may also be used to suppress alloimmune responses to transplantation antigens, i.e., host-versus-graft diseases (HVGDs), GVHDs and organ transplantations. An "alloimmune response" is one in which the immune system of an individual initiates and may propagate a primary and/or secondary response against the tissues, cells, or molecules of another, as, for example, in a transplant or transfusion. Alloimmune responses are induced by foreign histoincompatible alloantigens, expressed for example on the surface of transplanted tissue. AML patients frequently develop chronic GVHD following whole body irradiation and stem cell or bone marrow transfer.

In transplantation rejection, for example, the immune system of the tissue recipient recognizes these foreign histoincompatible alloantigens and attacks the transplanted organ, leading to its destructions. In GVHD, such as can occur after bone marrow transplantation, T cells present in the graft, either as contaminants or intentionally introduced into the host, attack the tissues of the transplant recipient after perceiving host tissues as antigenically foreign. The T cells produce an excess of cytokines, including TNF-α and IFN-γ. A wide range of host antigens can initiate graft-versus-host-disease, among them the human leukocyte antigens (HLAs). However, GVHD can occur even when HLA-identical siblings are the donors. HLA-identical siblings or HLA-identical unrelated donors often have genetically different proteins (called minor histocompatibility antigens) that can be presented by MHC molecules to the recipient's T-cells, which see these antigens as foreign and mount an immune response.

Toll-Like Receptor Signaling

As described in the Examples, the involvement of certain TLR signaling pathway adaptor proteins in the effect of small compounds on MDSC suppressive function was evaluated. Toll-like receptors (TLRs) are expressed on a wide variety of cells in mammals, including on cells of the innate and adaptive immune systems. In particular, TLRs are expressed on MDSCs [De Santo C et al., 2008, J Clin Invest. 118:4036-48]. Activation of TLRs leads to the induction of inflammatory responses and the development of antigen-specific adaptive immunity. [Reviewed in Takeda, K. et al. (2003) Annual Review of Immunology. 21:335-376].

Biochemical studies and genetic analyses using transgenic mice have revealed specific ligands for the activation of TLRs. Of the 11 TLRs described, the ligands for 10 of the receptors have been identified. TLR1, TLR2, TLR4 and TLR6 (both as heterodimers and homodimers) recognize different microbial structures, whereas TLR3 recognizes viral double stranded RNA (dsRNA). TLR4 recognizes lipopolysaccharide (LPS) from gram-negative bacteria. TLR5 recognizes Flagellin, a protein found in the flagella of gram-negative bacteria. TLR7 and 8 recognize endosomal single-stranded RNA (ssRNA) to detect infection by virus, and TLR9 detects unmethylated CpG motifs, characteristic of bacterial DNA. TLR11, present in mice, but not humans, senses the profilin-like proteins from the protozoan parasite *Toxoplasma gondii* and also recognizes uropathogenic *E. coli*.

TLRs are characterized by an extracellular domain composed of leucine-rich-repeat motifs for ligand binding as well as an IL-1 receptor domain (termed TIR domain). TLR intracellular domains specifically recruit several adaptor proteins including MyD88, TRIF, TIRAP/MAL, TOLLIP, and/or TRAM for downstream signaling. These adaptor proteins subsequently associate with a family of IL-1 receptor associated kinases (IRAK1, 2, M, and 4). Recruitment of numerous downstream signaling proteins leads to activation of a range of transcription factors such as NF-κB, AP-1, and IRFs (e.g., IRF-3), which are responsible for specific gene transcription, including the genes for pro-inflammatory cytokines including IL-6, IL-10, IL-17, and TGF-β. Recruitment also leads to activation of the MAP kinases, such as JNK, Erk and p38α,β. The Examples of the present invention show that the small compound GA inhibits the NFκB-dependent, LPS-driven induction of phosphorylated IRF-3.

While many of the TLR signaling pathways depend on the adaptor protein MyD88, some TLRs do not depend entirely, or at all, on MyD88. In these MyD88-independent pathways, the signal is transmitted through another adaptor molecule, TRIF. Studies using TRIF KO mice have determined which TLRs depend on TRIF for signaling (such as, e.g., TLR3). Studies using MyD88, TRIF double knockout mice, which express neither functional MyD88 nor TRIF proteins, have shown that all TLR signaling is completely abrogated in the absence of both of these proteins. [See, Kawai T and Akira S. (2007) Semin Immunol; 19:24-32; Medzhitov R. (2007) Nature; 449:819-26]. As described in the Examples, TRIF KO mice were used to determine the role of the TRIF pathway in the MDSC-mediated, small compound-enhanced induction of Treg cells.

TCR Transgenic Mice

T cell receptor (TCR) transgenic systems may be used to carry out proliferation assays. For example, CD4 T cells may be isolated from the spleen of a transgenic mouse that has T cells expressing a specific TCR. For example, an OVA TCR Transgenic (Tg) mouse has CD4 T cells which express a transgenic TCR gene encoding a TCR that is specific for OVA peptide. In the presence of an antigen presenting cell (APC) and OVA peptide, the OVA TCR Tg CD4 T cell exhibits a strong proliferative response, since every T cell is specific for the OVA peptide and is stimulated to proliferate. This proliferative response is said to be antigen-specific. Other examples of TCR Tg systems include HA TCR Tg T cells, which have a TCR that is specific for HA peptide ("PHA"). PHA is phytohaemagglutinin, a lectin found in plants, especially beans; used as a mitogen to trigger cell division in T-lymphocytes.

DSS-Induced Colitis In Vivo Model

In certain aspects, the invention is related to the treatment of IBDs. Mouse models of IBD are well known in the art, and may be used to model human IBDs. For example, dextran sodium sulfate (DSS) may be administered to mice to induce IBD. In this model, mice are fed with water containing 3.5% DSS from day 0 to day 11. Following treatment, mice develop colitis. The severity of colitis is quantified (assigned a clinical score) by assessing stool consistency, bleeding, and weight loss, which ranges from 0 (healthy) to 4 (maximal severity). Histologically, DSS produces submucosal erosions, ulceration, inflammatory cell infiltration and crypt abscess as well as epithelioglandular hyperplasia. Histopathological analysis typically reveals extensive crypt and epithelial cell damage, significant infiltration of granulocytes and mononuclear immune cells, and tissue edema, often accompanied with severe ulceration. [Kawada et al., 2007, World J. Gastroenterol. 13: 5581-5593; Okayasu et al., 1990, Gastroenterology 98:694-702]

Proliferation Assay

In certain embodiments of the invention, cell proliferation is quantified. To assess proliferation in vitro, a tritiated [3H]-thymidine assay may be used. In this assay, the radiolabeled thymidine is incorporated into dividing cells and the level of this incorporation, measured using a liquid scintillation counter, is proportional to the amount of cell proliferation. Other methods of measuring T cell proliferation may also be used, such as e.g., CFSE-based methods. CFSE consists of a fluorescent molecule containing a succinimydyl ester functional group and two acetate moieties. CFSE diffuses freely inside the cells and intracellular esterases cleave the acetate groups converting it to a fluorescent, membrane impermeable dye. This dye is not transferred to adjacent cells. CFSE is retained by the cell in the cytoplasm and does not adversely affect cellular function. During each round of cell division, relative fluorescence intensity of the dye is decreased by half. The fluorescence may be measured by flow cytometry, and used to determine the number of cell divisions.

Compositions

In certain aspects, the present invention provides compositions comprising MDSCs and small compounds. For example, compositions comprising MDSCs in combination with GA and/or a MAP kinase inhibitor are provided. In a preferred embodiment, MDSCs are administered with GA and a MAP kinase inhibitor. In some aspects, MDSCs are derived from bone marrow or HSCs in vitro. In another aspect, MDSCs are freshly isolated from a patient or donor, as described, supra. The MDSCs of the invention may be autologous or allogeneic. In yet other aspects of the invention, a subject or patient is administered a composition containing MDSCs and one or more small compounds of the invention. Administration may be achieved by any suitable method. In yet another aspect, a subject is administered MDSCs and one or more small compounds of the invention, each as a separate composition. For example, a subject may be administered one composition containing MDSCs and one or more compositions each containing one or more small compound, such as, e.g., GA and/or SP600125. Such compositions may be administered to at the same or different times via the same or different routes of administration.

In one aspect of the invention, a patient is administered a composition containing at least one stem cell mobilizer, such as, but not limited to G-CSF, AMD 3100, CTCE-9908, FTY720, Flt3 ligand, SCF, S100A9, GM-CSF and M-CSF. The patient is further administered one or more additional compositions containing one or more small compounds of the invention for enhancing the suppressive activity of MDSCs, such as GA and/or SP600125. In certain aspects of the invention, these compositions may be administered at the same or different times and at the same or different sites. In another aspect, stem cell mobilizing agents and small compounds of the invention may be administered as a single composition.

The compositions of the invention can be formulated for administration in any convenient way for use in human or veterinary medicine. The MDSCs of the invention may be incorporated into liposomes, microemulsions, micelles, unilamellar or multilamellar vesicles, erythrocyte ghosts or spheroblasts. In one embodiment, the MDSCs, stem cell mobilizing agents and/or small compounds of the invention can be delivered in one or more vesicles, including as a liposome (see Langer, Science, 1990; 249:1527-1533; Treat et al., in Liposomes in the Therapy of Infectious Disease and Cancer, Lopez-Berestein and Fidler (eds.), Liss: New York, pp. 353-365 (1989); Lopez-Berestein, ibid., pp. 317-327; see generally ibid.).

In yet another embodiment, MDSCs and small compounds of the invention can be delivered in a controlled release form. For example, one or more small compounds (e.g., GA and/or SP600125) may be administered in a polymer matrix such as poly (lactide-co-glycolide) (PLGA), in a microsphere or liposome implanted subcutaneously, or by another mode of delivery (see, Cao et al., 1999, Biomaterials, February; 20(4):329-39). Another aspect of delivery includes the suspension of the compositions of the invention in an alginate hydrogel.

The term "therapeutically effective" when applied to a dose or an amount refers to that quantity of a compound or pharmaceutical composition that is sufficient to result in a desired activity upon administration to a mammal in need thereof. As used herein, the term "therapeutically effective amount/dose" refers to the amount/dose of a pharmaceutical composition of the invention that is suitable for treating a patient or subject having an autoimmune disease. In certain embodiments of the invention the patient or subject may be a mammal In certain embodiments, the mammal may be a human.

The present invention also provides pharmaceutical formulations or dosage forms for administration to mammals in need thereof.

The subject invention also concerns the use of GA or a GA derivative and/or MAP kinase inhibitors, such as, e.g., SP600125, in the preparation of a pharmaceutical composition. In some embodiments, a pharmaceutical composition of the invention includes MDSCs and GA and/or a small compound inhibitor of a MAP kinase. In a specific embodiment, the inhibitor is a small compound inhibitor of JNK. In yet another embodiment, the pharmaceutical composition includes MDSCs, GA and a small compound MAP kinase inhibitor. The pharmaceutical compositions of the invention optionally include a pharmaceutically acceptable carrier or diluent.

When formulated in a pharmaceutical composition, the compositions of the present invention can be admixed with a pharmaceutically acceptable carrier or excipient. The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicles with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Alternatively, the carrier can be a solid dosage from carrier, including but not limited to one or more of a binder (for compressed pills), an encapsulating agent, a flavorant, and a colorant. Suitable pharmaceutical carriers are described in "Remington's Pharmaceutical Sciences" by E. W. Martin.

The compositions of the present invention can be formulated into any form known in the art using procedures available to one of skill in the art. The compositions of the present invention may be mixed with other food forms and consumed in solid, semi-solid, suspension or emulsion form. In one embodiment, the composition is formulated into a capsule or tablet using techniques available to one of skill in the art. However, the present compositions may also be formulated in another convenient form, such as an injectable solution or suspension, a spray solution or suspension, a lotion, a gum, a lozenge, a food or snack item. Food, snack, gum or lozenge items can include any ingestible ingredient, including sweeteners, flavorings, oils, starches, proteins, fruits or fruit extracts, vegetables or vegetable extracts, grains, animal fats or proteins. Thus, the present compositions can be formulated into cereals, snack items such as chips, bars, gum drops, chewable candies or slowly dissolving lozenges. The compositions of the present invention can also be administered as dry powder or metered dose of solution by inhalation, or nose-drops and nasal sprays, using appropriate formulations and metered dosing units.

In a specific embodiment, a pharmaceutical composition of the invention comprises: MDSCs in combination with GA or SP600125 alone, or MDSCs in combination with GA and SP600125, and a pharmaceutically acceptable carrier or diluent for intravenous or subcutaneous administration. In yet another specific embodiment of the invention, a pharmaceutical composition of the invention comprises GA and/or SP600125 and a pharmaceutically acceptable carrier or diluent, and another pharmaceutical composition comprises MDSCs or one or more stem cell mobilizers. In still another embodiment, MDSCs, GA and/or a MAP kinase inhibitor, such as SP600125, are each administered separately to a patient in need of treatment as separate pharmaceutical compositions. In yet another embodiment, at least one stem cell mobilizer, and GA and/or a MAP kinase inhibitor, such as SP600125, are each administered separately to a patient in need of treatment as separate pharmaceutical compositions. Any of the pharmaceutical compositions of the invention may be administered separately or together, at the same or different sites, at the same or different times, and according to the same or different frequencies of administration.

In certain aspects of the invention, MDSCs are pre-treated in vitro with GA or a MAP kinase inhibitor alone or with GA and a MAP kinase inhibitor. The pre-treated MDSCs may then be administered to a patient in need of treatment. The effective amounts of GA and MAP kinase inhibitor for in vitro treatment of MDSCs may be readily determined by the skilled artisan without undue experimentation. In a titration experiment, the amount of GA and/or MAP kinase inhibitor that is effective for maintaining the MDSC in an immature state in the presence of the activator lipopolysaccharide (LPS) and is not toxic to the MDSC may be determined and selected for use.

Administration

The compositions and formulations of the present invention can be administered topically, parenterally, orally, by inhalation, as a suppository, or by other methods known in the art. The term "parenteral" includes injection (for example, intravenous, intraperitoneal, epidural, intrathecal, intramuscular, intraluminal, intratracheal or subcutaneous). The preferred routes of administration are intravenous (i.v.), intraperitoneal (i.p.) and subcutaneous (s.c.) injection. When MDSCs are administered separately from the small compounds of the invention, the preferred route of administration is i.v. However, MDSCs may also be administered subcutaneously or intraperitoneally. The preferred route of administration for GA and the stem cell mobilizers of the invention is subcutaneous administration. The preferred route of administration for SP600125 is i.p. injection. However, the stem cell mobilizers and small compounds of the invention may be administered in any convenient way, including for i.v., s.c., oral, or i.p. injection.

Administration of the compositions of the invention may be once a day, twice a day, or more often, but frequency may be decreased during a maintenance phase of the disease or disorder, e.g., once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art. More generally, dose and frequency will depend in part on recession of pathological signs and clinical and subclinical symptoms of a disease condition or disorder contemplated for treatment with the present compounds.

The MDSC and small compound compositions described herein can be used to treat autoimmune diseases and alloimmune responses. In certain embodiments, the compositions of the invention are useful for the treatment of transplant rejection.

It will be appreciated that the amount of MDSCs and small compounds of the invention required for use in treatment will vary with the route of administration, the nature of the condition for which treatment is required, and the age, body weight and condition of the patient, and will be ultimately at the discretion of the attendant physician or veterinarian. These compositions will typically contain an effective amount of the compositions of the invention, alone or in combination with an effective amount of any other active material, e.g., those described above. Preliminary doses can be determined according to animal tests, and the scaling of dosages for human administration can be performed according to art-accepted practices.

Keeping the above description in mind, typical dosages of MDSCs for administration to humans range from about $5 \times 10^5$ to about $5 \times 10^6$ or higher, although lower or higher numbers of MDSCs are also possible. In embodiments in which autologous MDSCs are administered, an advantage of the present invention is that there is little to no toxicity, since the MDSCs are autologous. In a preferred embodiment, a patient may receive, for example, $5 \times 10^7$-$5 \times 10^{10}$ MDSCs.

Keeping the above description in mind, typical dosages of GA for administration to humans may range from about 50 µg/kg (of body weight) to about 50 mg/kg per day. A preferred dose range is on the order of about 100 µg/kg/day to about 10 mg/kg/day, more preferably a range of about 300 µg/kg/day to about 1 mg/kg/day, and still more preferably from about 300 µg/kg/day to about 700 µg/kg/day.

The length of treatment, i.e., number of days, will be readily determined by a physician treating the patient, however the number of days of treatment may range from 1 day to about 20 days. In a preferred embodiment, the dose of GA is administered at a frequency of about once every 7 days to about once every day. In a more preferred embodiment, the dose of GA is administered at a frequency of about once every day. Preferably, the number of days of treatment is from about 5 to about 15 days and most preferably from about 10 to about 12 days. In a specific embodiment, a patient may receive, for example, 500 µg/kg/day subcutaneously (SC) for 12 days. In another embodiment of the invention, the dose of GA is administered at a frequency of about once every 30 days to about once every day. In a specific embodiment, GA is administered subcutaneously for 12 days. [See, Weber, M. S., et al., (2007) Nat. Med.; 13(8):935-943.]

Keeping the above description in mind, typical dosages of SP600125 for administration to humans range from 50 µg/kg (of body weight) to about 500 mg/kg per day. A preferred dose is about 50 mg/kg/day.

Keeping the above description in mind, typical dosages of the stem cell mobilizer Flt3 ligand may range from about 10 µg/kg to about 1000 µg/kg. A preferred dose range is on the order of about 20 µg/kg to about 300 µg/kg. In certain embodiments, a patient may receive, for example, 20 µg/kg of Flt3L per day subcutaneously for 14 days each month [see Disis, M L et al. (2002) Blood. 99: 2845-2850]. Preferably, the length of treatment is at least 5 days.

Keeping the above description in mind, typical dosages of G-CSF may range from about 2 to about 12 mg/kg/day. The length of treatment may range from about 1 day to about 14 days. Preferably, the length of treatment is at least 5 days.

Methods of Treatment

The present invention provides for the use of MDSCs in combination with small compounds, such as GA and MAP kinase inhibitors, to treat autoimmune diseases, alloimmune responses, or any other disease, disorder or condition that involves a T cell response. Generally, these are conditions in which the immune system of an individual (e.g., activated T cells) attacks the individual's own tissues and cells, or implanted tissues, cells, or molecules (as in a graft or transplant). Exemplary autoimmune diseases that can be treated with the methods of the instant disclosure include type I diabetes, multiple sclerosis, thyroiditis (such as Hashimoto's thyroiditis and Ord's thyroiditis), Grave's disease, systemic lupus erythematosus, scleroderma, psoriasis, arthritis, rheumatoid arthritis, alopecia greata, ankylosing spondylitis, autoimmune hemolytic anemia, autoimmune hepatitis, Behcet's disease, Crohn's disease, dermatomyositis, glomerulonephritis, Guillain-Barre syndrome, IBD, lupus nephritis, myasthenia gravis, myocarditis, pemphigus/pemphigoid, pernicious anemia, polyarteritis nodosa, polymyositis, primary biliary cirrhosis, rheumatic fever, sarcoidosis, Sjogren's syndrome, ulcerative colitis, uveitis, vitiligo, and Wegener's granulomatosis. Exemplary alloimmune responses that can be treated with the methods of the instant disclosure include GVHD and transplant rejection.

In accordance with the present invention, there may be employed conventional molecular biology, microbiology, recombinant DNA, immunology, cell biology and other related techniques within the skill of the art. See, e.g., Sambrook et al., (2001) Molecular Cloning: A Laboratory Manual. 3rd ed. Cold Spring Harbor Laboratory Press: Cold Spring Harbor, N.Y.; Sambrook et al., (1989) Molecular Cloning: A Laboratory Manual. 2nd ed. Cold Spring Harbor Laboratory Press: Cold Spring Harbor, N.Y.; Ausubel et al., eds. (2005) Current Protocols in Molecular Biology. John Wiley and Sons, Inc.: Hoboken, N.J.; Bonifacino et al., eds. (2005) Current Protocols in Cell Biology. John Wiley and Sons, Inc.: Hoboken, N.J.; Coligan et al., eds. (2005) Current Protocols in Immunology, John Wiley and Sons, Inc.: Hoboken, N.J.; Coico et al., eds. (2005) Current Protocols in Microbiology, John Wiley and Sons, Inc.: Hoboken, N.J.; Coligan et al., eds. (2005) Current Protocols in Protein Science, John Wiley and Sons, Inc.: Hoboken, N.J.; Enna et al., eds. (2005) Current Protocols in Pharmacology John Wiley and Sons, Inc.: Hoboken, N.J.; Hames et al., eds. (1999) Protein Expression: A Practical Approach. Oxford University Press: Oxford; Freshney (2000) Culture of Animal Cells: A Manual of Basic Technique. 4th ed. Wiley-Liss; among others. The Current Protocols listed above are updated several times every year.

EXAMPLES

The present invention is described further below in working examples which are intended to further describe the invention without limiting the scope therein.

In the examples below, the following materials and methods were used.

Mice

All mice used are commercially available and were obtained from The Jackson Laboratory (Bar Harbor, Me.).

Isolation of MDSCs and Normal Monocytes

For isolation of MDSCs, mice with tumor sizes greater than $10 \times 10$ mm$^2$ were sacrificed and their spleen, tibias, and femurs were harvested and cell suspensions were prepared from these tissues. Normal monocytes were isolated from the bone marrow of naive Balb/c mice and a cell suspension was prepared. Following preparation of cells suspensions and lysis of red blood cells (RBC), the cells were cultured overnight in RPMI-1640 medium (Sigma-Aldrich), and the cells were fractionated by centrifugation on a Percoll (Amersham Biosciences, Uppsala, Sweden) density gradient as described. Cells were collected from the gradient interfaces. Cell bands between 40% and 50% were labeled as fraction 1, between 50% and 60% as fraction 2, and between 60% and 70% as fraction 3. Fraction 2 cells were incubated with anti-CD115 PE-conjugated antibody in staining buffer (PBS, 2% FCS, 0.1% azide) for 15 minutes, cells were washed with PBS three times, and then anti-PE microbeads (Miltenyi Biotec) were added to the cells for 15 minutes. CD115 positive cells were selected by autoMACs cell separator (Miltenyi Biotec). The purity of the purified cells was checked by flow cytometry and populations that were >95% pure were chosen for the experiments described herein.

Splenocyte and Mesenteric Lymph Node (MLN) Proliferation Assays

Splenocytes from CD4+ HA-TCR transgenic mice were cultured in the presence of serial dilutions (splenocyte: MDSC ratios=1:1, 1:0.5, 1:0.25, 1:0.125) of irradiated MDSCs in the absence or presence of SP600125, GA, or both. [3H]-thymidine was added during the last 8 hours of 72-hour culture.

On day 11 after IBD induction, mice were terminated, and MLN cells were isolated and cultured in the presence or absence of PHA. [3H]-thymidine was pulsed during the last 8 hours of 72-hour culture for the measurement of T cell proliferation.

Treg Cell Induction Assays

Splenocytes from CD4+ HA-TCR transgenic mice were co-cultured with irradiated MDSCs at a ratio of 4:1 in the absence or presence of GA, SP600125, or both. Five days later, the viable cells were harvested and used for intracellular staining of Foxp3 (upper panel) or analysis of Foxp3 gene expression by RT-PCR (lower panel). For staining, cells were incubated with anti-CD4-FITC and anti-CD25-APC followed by intracellular staining with anti-Foxp3-PE per the manufacturer's instructions. Cells stained with isotype-matched antibodies were used as controls. An aliquot of cells was used for total RNA isolation and the expression of Foxp3 was assessed by RT-PCR.

RT-PCR Analysis

Gene expression of FoxP3 was determined by RT-PCR using primers having the following sequences:

MDSC Differentiation Assay

Gr-1+CD115+ MDSCs were sorted by MACS and cultured in the absence or presence of GA, SP600125, or both. Twenty-four hours later, viable cells were harvested and stained with anti-CD86, anti-CD80, anti-CD11c, anti-I-A, anti-F4/80, or isotype-matched control followed by flow cytometric analysis to assess MDSC differentiation.

Adoptive Transfer of MDSCs

For adoptive transfer of MDSCs, $5 \times 10^6$ purified MDSCs suspended in PBS were administered by intravenous infusion at day 0 and day 7.

DSS-Induced Colitis—In Vivo Model

Mice were left untreated or treated with sorted MDSCs ($5 \times 10^6$ cells/mouse) alone or in combination with GA and/or SP600125 (Sigma-Aldrich), on the day of disease induction. C57BL/6 mice were fed with water containing 3.5% DSS from day 0 to day 11. Mice were injected intraperitoneally with SP600125 or subcutaneously with GA or control PBS from day 0 to day 11. Some mice also received adoptive transfer of MDSCs in PBS ($5 \times 10^6$ cells/mouse) via tail vein on days 0 and 7. The severity of colitis was quantitated as a clinical score by assessing stool consistency, bleeding, and weight loss, which ranges from 0 (healthy) to 4 (maximal severity). The clinical score (weight loss, stool consistency, and bleeding) of treated mice was assessed in a double-blind fashion.

Isolation and Histological Analysis of Colons

On day 11 post-IBD induction, colon tissues from treated mice were removed, fixed in 3% formaldehyde, sectioned, and stained with H&E staining to determine the pathology score of colitis. To reflect the general condition of the mice, a disease activity index (DAI) was determined by an investigator blinded to the protocol by scoring the extent of body weight loss, stool guaiac positivity or gross bleeding, and stool consistency according to the method described in Murthy et al. (1993) "Treatment of Dextran Sulfate Sodium-Induced Murine Colitis by Intracolonic Cyclosporin," *Digest. Dis. Sci.;* 38(9):1722-1734. Briefly, animals were weighed before starting DSS administration and on the day when animals were killed. Stool consistency and the degree of blood in stool were evaluated on the day when animals were killed. The entire colon then was removed and length were measured, include the rectum, transverse colon, and caecum.

| Primer | Sequence |
|---|---|
| FOXP3 (sense) | 5'-CAGCTGCCTACAGTGCCCCTAG-3' (SEQ ID NO: 1) |
| FOXP3 (antisense) | 5'-CATTTGCCAGCAGTGGGTAG-3' (SEQ ID NO: 2). |

Normal Monocyte Assay

CD115+ MDSCs and normal CD115+ monocytes were isolated from the bone marrows of tumor-bearing and naive Balb/c mice, respectively, and were co-cultured with CD4 OTII TCR transgenic splenocytes at a ratio of 1:4 in the absence or presence of GA, SP600125, or both. Five days later, the viable cells were harvested and stained with anti-CD4-FITC+anti-CD25-APC+anti-Foxp3-PE or isotype controls followed by flow cytometric analysis.

Cytokine Production by MDSCs

Sorted Gr-1+CD115+ MDSCs from tumor-bearing mice were stimulated with IFN-γ in the absence or presence of GA, SP600125, or both. Twenty-four hours after stimulation, culture supernatants were collected and the concentrations of IL-10, TGF-β, IL-6, and IL-23 were determined by ELISA (R&D Systems).

The segment of colon were opened longitudinally and fixed in 10% neutral buffered formalin prior to histological processing. Haematoxylin and eosin (H-E)-stained sections were examined microscopically. To evaluate the severity of inflammation, 15 randomly selected fields (magnification ×100) were inspected in each section by a pathologist blinded to the treatment protocol and graded as follows: grade 0, normal colonic mucosa; grade 1, loss of one-third of the crypts; grade 2, loss of two-thirds of the crypts; grade 3, lamina propria covered with a single layer of epithelial cells with mild inflammatory cell infiltration; and grade 4, erosions and marked inflammatory cell infiltration. After grading the 15 fields, the mean grade was calculated for each section and expressed as histological score. The severity of colitis was quantified as the clinical score by assessing stool consistency, bleeding, and weight loss, which ranges from 0 (healthy) to 4 (maximal severity). The clinical score (weight loss, stool consistency, and bleeding) of treated mice was assessed in a double-blind fashion.

In Vitro Colon Incubation for Measurement of Cytokine Release

In the IBD model, colonic inflammation was assessed by measurement of cytokine release. On day 11 after IBD induction, colons were removed and processed to determine the concentration of IFN-γ, IL-17A, IL-10, and TGF-β by ELISA. Mice were sacrificed and the colon was sectioned, a single-cell suspension was prepared from the sections by grinding them between glass slides. Cells were plated in 3 ml culture medium in 6-well tissue culture plates (Becton Dickinson). The cells were incubated for 24 hours and then culture supernatants were collected for ELISA. All ELISA reagents were from R&D Systems®.

Western Blot Analysis of MDSCs

The effect of GA on the components (NF-κB and IRF-3) of the TLR4-LPS signaling pathway was analyzed by Western blot analysis of protein samples from MDSCs stimulated with control (culture media), GA alone, LPS, or GA+LPS for 2 hours. Actin was used as a loading control. Primary antibodies were anti-NFκB, anti-phospho-IRF3 (pIRF3), and anti-β-actin (Cell Signaling Technologies, Danvers, Mass.).

In Vivo MDSC Mobilization Assay Using Flt3 Ligand and G-CSF

Naïve mice were injected with PBS control or Flt3-L (2 μg/day) plus G-CSF (2 μg/day) for 5 consecutive days. The numbers of MDSCs in the blood, spleen, and bone marrow were quantified on day 7 by flow cytometric analysis.

In Vivo Treatment with GA and SP600125

GA was given subcutaneously at a dose of 600 μg/mouse, daily, and SP600125 in PBS was administered intraperitoneally at a dose of 50 mg/kg/body weight daily continuously for 11 days.

EXAMPLE 1

The Effects of GA and SP600125 on the Suppressive Functions of MDSCs

To determine whether GA and SP600125 could further enhance MDSC suppressive function, Gr-1+CD115+ MDSCs were sorted from bone marrow and spleens of tumor-bearing mice and the suppressive activity against HA peptide-mediated-T-cell proliferation was assessed in the presence or absence of GA and SP600125. As shown in FIG. 1A, the highest suppressive effect was observed in the presence of both GA and SP600125, when compared with untreated MDSCs, GA, or SP600125 alone treated MDSCs. The result indicates that the suppressive activity of MDSCs can be further increased by treatment with GA and SP600125.

Figure 1B:
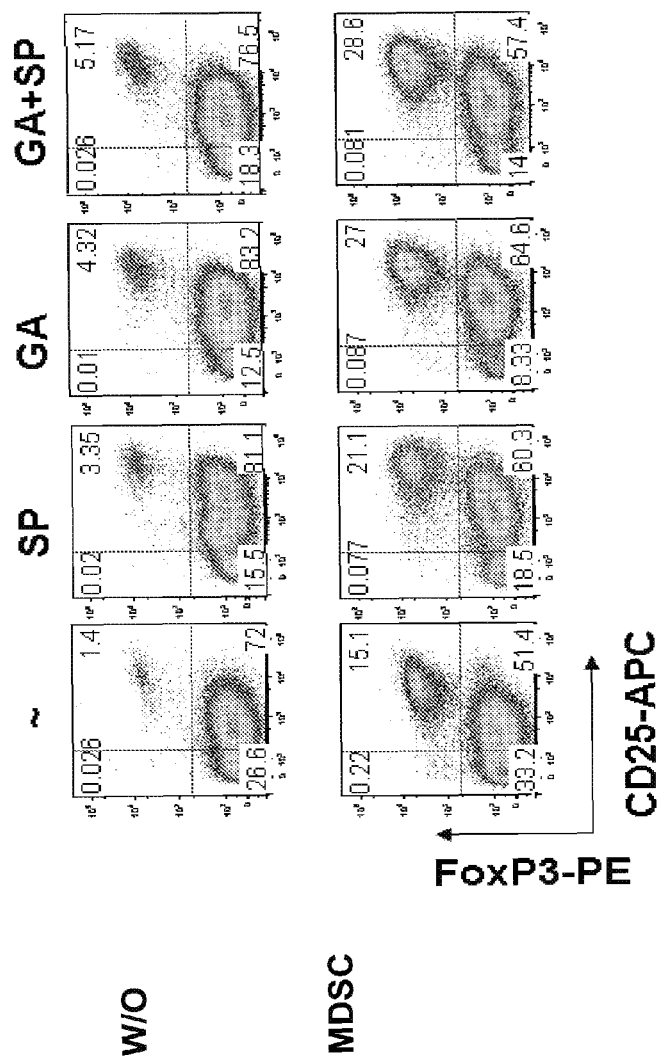
FIG. 1B. Flow cytometric data expressed as cell plots showing the expression of FoxP3 and CD25 in MDSCs following treatment with control (~), SP, GA, or GA+SP.
Figure 1C:
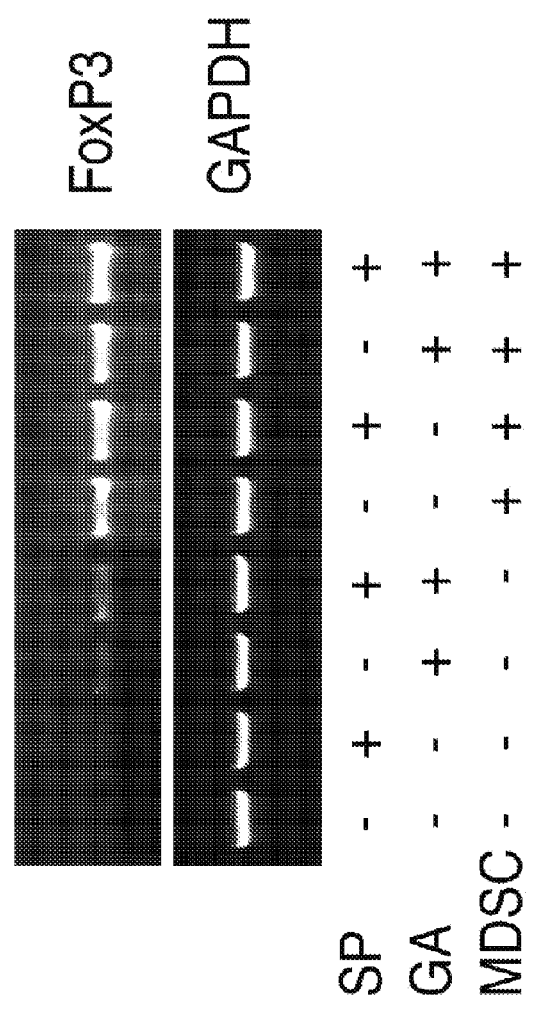
FIG. 1C. Agarose gel resolving the PCR products from the indicated experimental groups showing the expression of FoxP3 and GAPDH (housekeeping control gene).

It was next evaluated whether GA and SP600125 could increase the Treg cell inducing activity, another suppressive mechanism mediated by MDSCs. Splenocytes from CD4+ HA-TCR transgenic mice were co-cultured with irradiated MDSCs at a ratio of 4:1 in the absence or presence of GA, SP600125, or both. Five days later, the viable cells were harvested and used for intracellular staining of Foxp3 (FIG. 1B) or analysis of Foxp3 gene expression by RT-PCR (FIG. 1C). As shown in FIG. 1B, the treatment with both SP600125 and GA significantly increased the percentage of CD4+ CD25+Foxp3+ Treg cells in the co-culture with MDSCs. The result of Foxp3 gene expression assessed by RT-PCR was consistent with the intracellular staining of Foxp3 (FIG. 1C).

Figure 2:
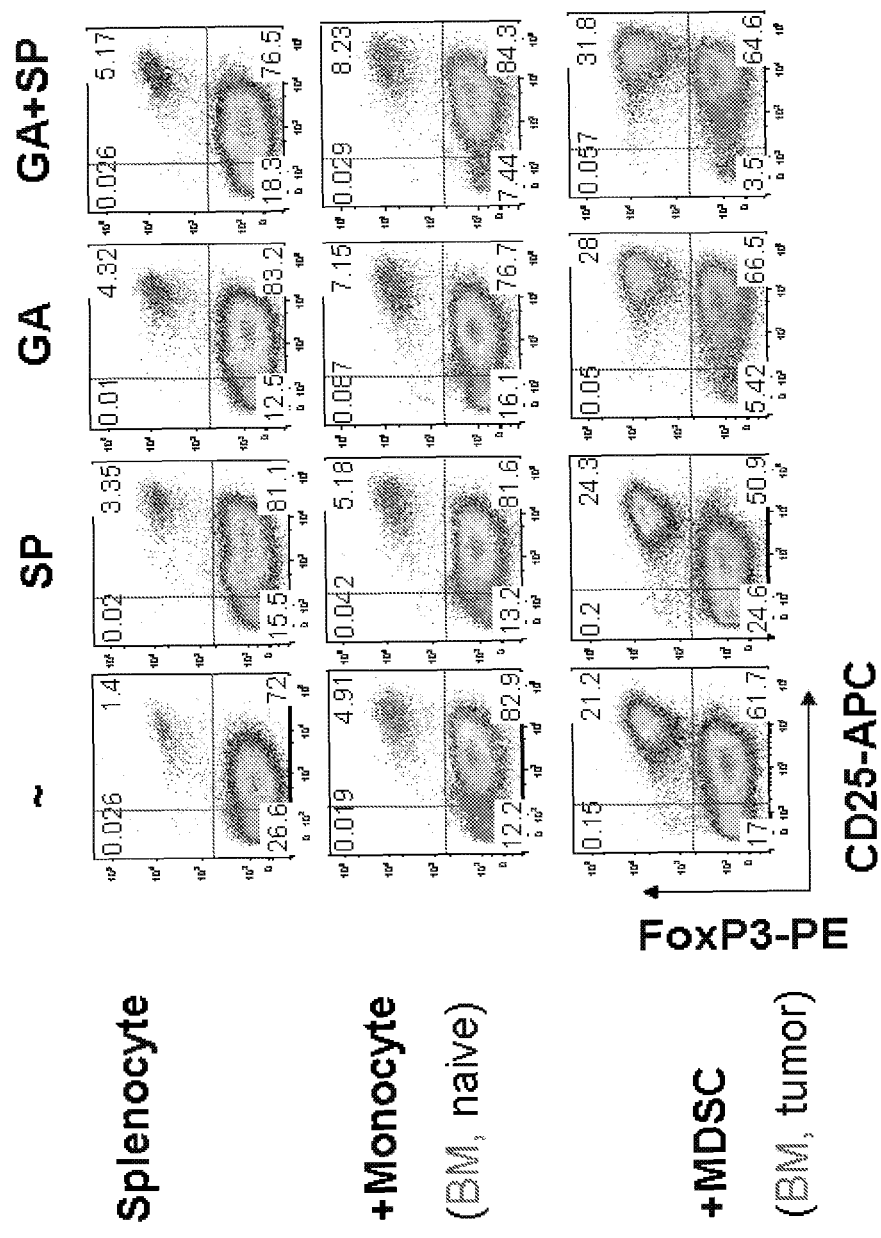
FIG. 2. Flow cytometric data expressed as cell plots show that normal CD115+ monocytes are inefficient in inducing Treg cell development in the presence or absence of GA and SP600125 when compared to MDSCs isolated from tumor-bearing mice.

To verify whether the enhancement of suppressive activities (suppression of T-cell proliferation and Treg cell induction) by GA and SP600125 is specific to MDSCs, the Treg cell inducing activity of normal CD115+ monocytes from naive mice was analyzed in the presence of GA and SP600125. Naïve splenic CD115+ monocytes exhibited no significant Treg cell inducing activity (FIG. 2). GA and SP600125, alone or in combination, slightly increased the percentage of CD4+ CD25+Foxp3+ Treg cells in the co-culture with normal monocytes when compared to the culture without normal monocytes or MDSCs (8.23% vs. 5.17%). But the percentage of Treg cells was drastically lower when compared to MDSCs alone or in the presence of GA and SP600125 (8.23% vs. 21.2% vs. 31.8%, respectively). The data indicate that MDSCs are superior to normal monocytes in the induction of Treg cell development, and the combination of GA and SP600125 enhanced MDSCs' ability to induce Treg cells (FIG. 2).

Figure 3A:
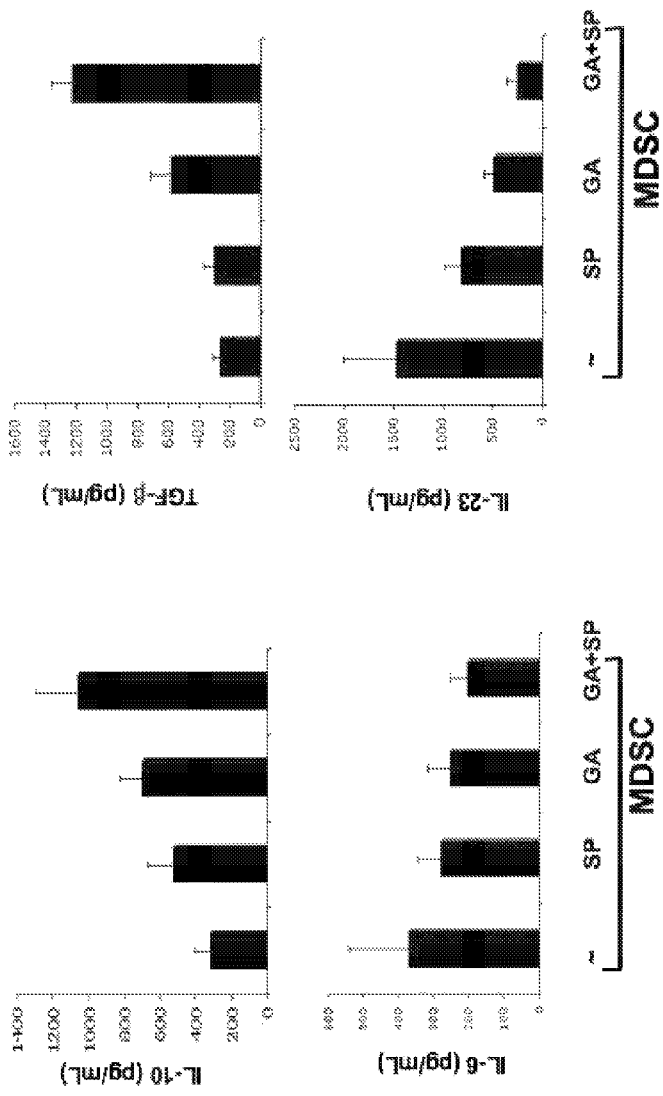
FIG. 3A. Bar graphs showing that GA and SP600125 increase the secretion of IL-10 and TGF-β, but decrease the secretion of IL-6 and IL-23 by MDSCs.

It was next determined whether GA, SP600125, or both exert an effect on cytokine production by MDSCs. Sorted Gr-1+CD115+ MDSCs from tumor-bearing mice were stimulated with IFN-γ in the absence or presence of GA, SP600125, or both. Twenty-four (24) hours after stimulation, culture supernatants were collected and the concentrations of IL-10, TGF-β, IL-6, and IL-23 were determined by ELISA (R&D Systems®). GA or SP600125 alone was capable of enhancing the secretion of IL-10 and TGF-β while decreasing IL-6 and IL-23 production by MDSCs in vitro (FIG. 3A). The effect was synergistically increased by the combination of GA and SP600125.

Figure 3B:
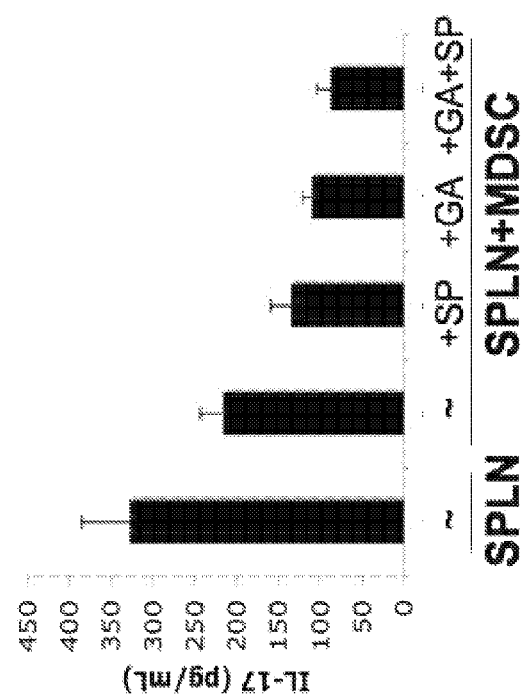
FIG. 3B. Bar graphs showing the synergistic effect of GA and SP600125 on the suppression of Th17 response by MDSCs.

Because IL-23 (p40/p19) is essential for the Th17 response, the effects of MDSCs, in the presence of GA, SP600125, or both, on IL-17A expression by CD4+ HA-TCR transgenic splenocytes stimulated with HA peptides was determined. Splenocytes from CD4+ HA-TCR transgenic mice were co-cultured with irradiated MDSCs at the ratio of 3:1 in the presence of HA peptide and SP600125, GA, or a combination of both. Five days later, the culture supernatants were collected for the determination of IL-17A concentration by ELISA. The result shows that MDSCs with GA or SP600125 alone or with a combination of GA and SP600125 decreased IL-17A production (FIG. 3B).

EXAMPLE 2

GA and SP600125 Cooperate in the Inhibition of MDSC Differentiation In Vitro

Figure 4A:
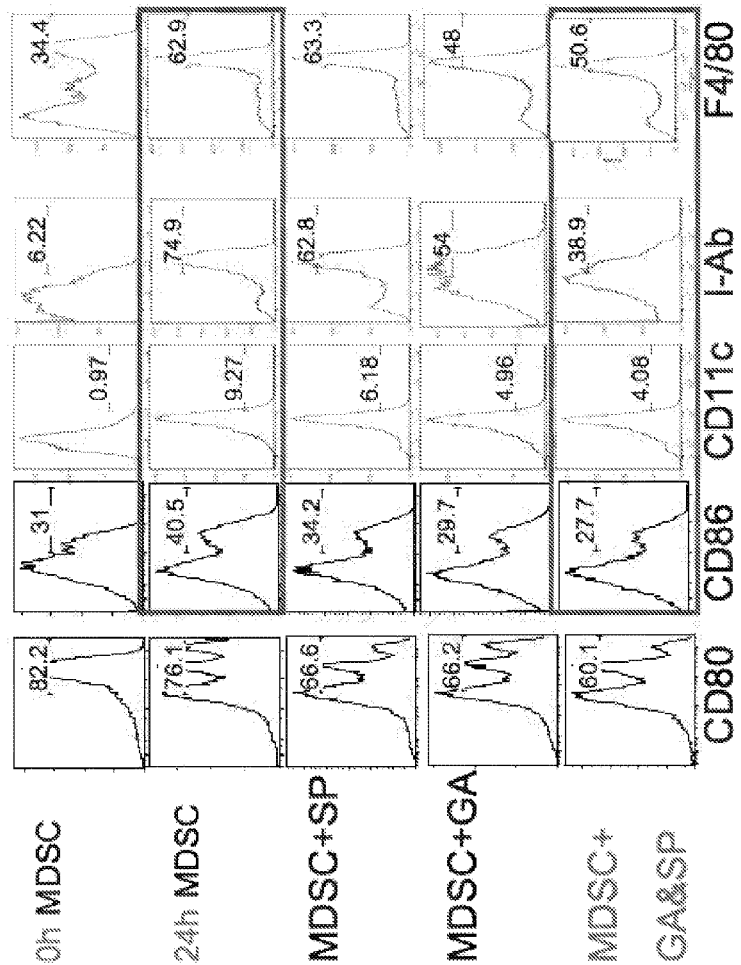
FIG. 4A. Flow cytometric data expressed as histograms showing that small compounds GA and SP600125 retard MDSC differentiation.

To test whether differentiation of MDSCs can be inhibited or retarded by the treatment of GA, SP600125, or both, Gr-1+ CD115+ MDSCs were sorted by MACS and cultured in the absence or presence of GA, SP600125, or both. Twenty-four (24) hours later, viable cells were harvested and stained with anti-CD86, anti-CD80, anti-CD11c, anti-I-A, anti-F4/80, or isotype-matched control followed by flow cytometric analysis. As shown in FIG. 4A, sorted Gr-1+CD115+ MDSCs spontaneously differentiated into CD11c+, CD86+ and IA/IE (MHC class II)+ cells and F4/80+ cells upon culture for 24 hours in the absence of cytokine or chemokine stimulation. Treatment with GA or SP600125 impaired the spontaneous differentiation of MDSCs, as evidenced by the lower expressions of CD11c, MHC class II, co-stimulatory molecules, and F4/80. Treatment with a combination of GA and SP600125 further retarded the differentiation of MDSCs. The result demonstrated that GA and SP600125 may sustain and enhance the suppressive functions of MDSCs by retaining the MDSCs at an immature phenotype.

It was further investigated whether the delay of MDSC differentiation correlated with the prolongation of the Treg cell inducing activity mediated by MDSCs. Purified Gr-1+ CD115+ MDSCs from tumor-bearing mice were left non-treated or treated with SP600125, GA, or a combination of both for 0, 48, and 96 hours followed by co-culture with CD4 HA TCR transgenic for an additional 5 days. Viable cells were harvested and stained with anti-CD4-FITC, anti-CD25-APC, and anti-Foxp3-PE or with isotype controls. The percentages of Treg cell subpopulations were determined by flow cytometry.

Figure 4B:
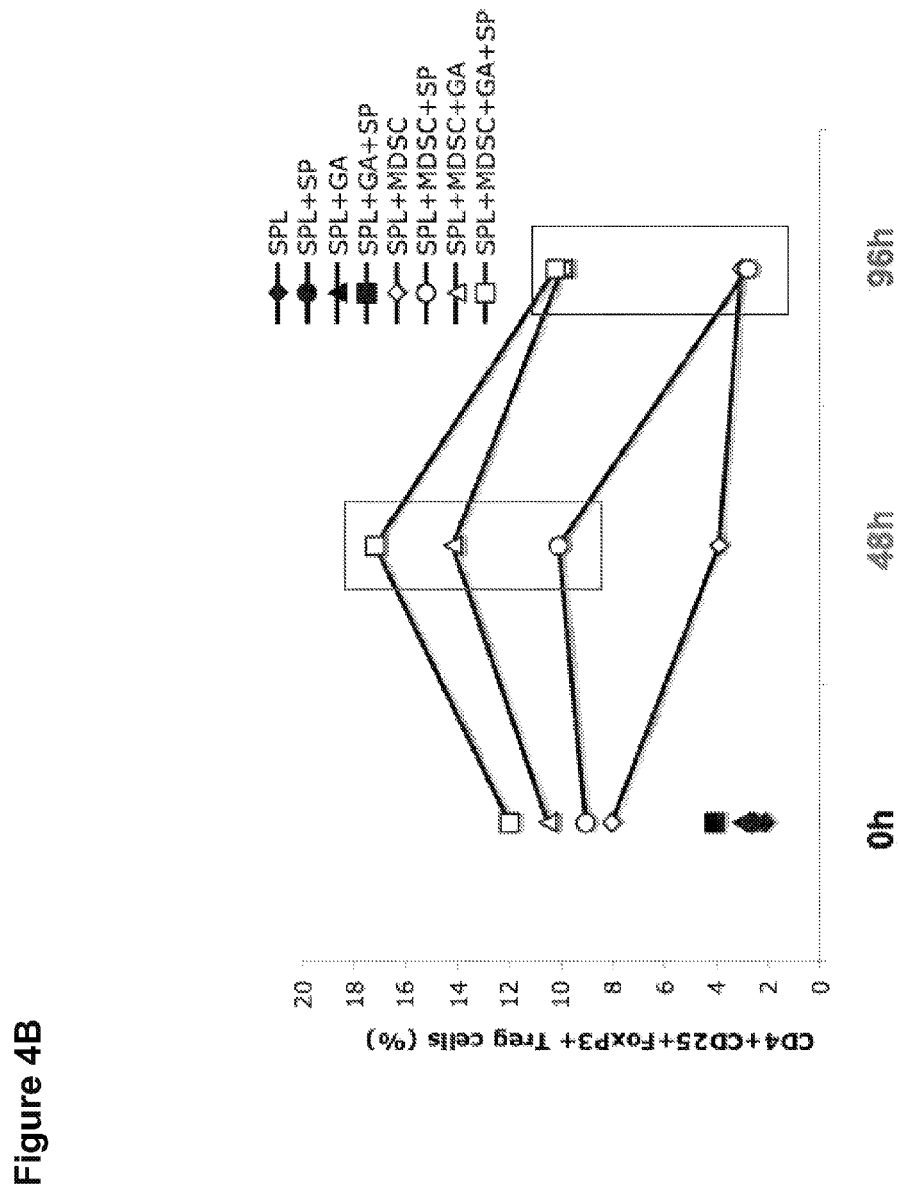
FIG. 4B. Graph depicting percentage of Treg cells in cell culture at indicated time points following culture with or without indicated combinations of MDSCs, GA and SP600125.

In the absence of treatment with GA or SP00125, the Treg cell inducing activity of MDSCs gradually waned over the period of 4-day culture (FIG. 4B). In contrast, SP600125 treated MDSCs still had the same Treg cell inducing activity as fresh-isolated MDSCs on Day 2, but lost this activity on day 4 of in vitro culture. Importantly, MDSCs treated with GA alone or in combination with SP600125 still maintained a significant Treg cell inducing activity even after 4 days of culture. The results indicate that the treatment of GA and SP600125 can not only delay the spontaneous differentiation of MDSCs upon removal from the tumor microenvironment, but also significantly prolong the Treg cell inducing activity of MDSCs.

EXAMPLE 3

The Therapeutic Effect of MDSCs in Combination Wwth the Treatment of GA and SP600125 in a Murine Model of Inflammatory Bowel Disease The therapeutic potential of MDSCs in combination with SP600125 and GA was assessed in a model of DSS (dextran sodium sulfate)-induced IBD. The ability of MDSCs and GA and SP600125 to suppress DSS-induced colitis was tested. Mice were left untreated or treated with sorted MDSCs ($5 \times 10^6$ cells/mouse) alone or in combination with GA, SP600125, or both on the day of disease induction. C57BL/6 mice were fed with water containing 3.5% DSS from day 0 to day 11. Mice were injected intraperitoneally with SP600125 (5 μM for i.p. injection) or subcutaneously with 600 μg/kg GA or control PBS from day 0 to day 11. Some mice also received adoptive transfer of MDSCs ($5 \times 10^6$ cells/mouse) via tail vein on days 0 and 7.

Figure 5A:
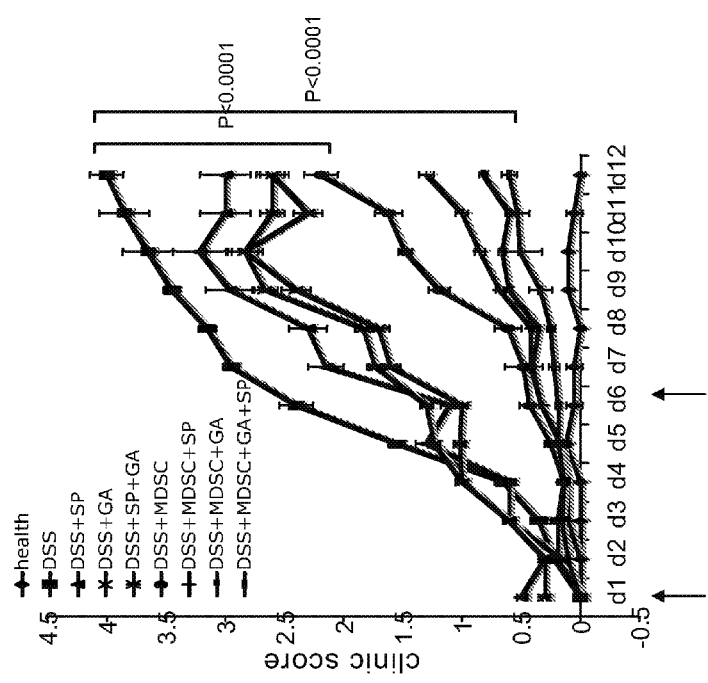
FIG. 5A. Graph of clinical scores of mice with DSS-induced colitis following treatment of mice with indicated combinations of MDSCs, GA and SP600125.
Figure 5B:
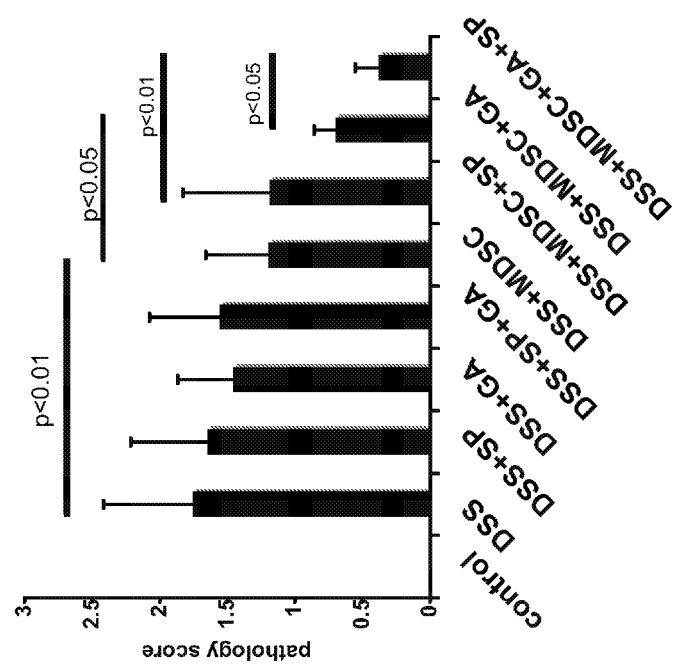
FIG. 5B. Graph of pathology scores with double blind diagnosis of mice with DSS-induced colitis following treatment of mice with indicated combinations of MDSCs, GA and SP600125.

The severity of colitis was quantified as the clinical score by assessing stool consistency, bleeding, and weight loss, which ranges from 0 (healthy) to 4 (maximal severity). The clinical score (weight loss, stool consistency, and bleeding) of treated mice was assessed in a double-blind fashion. The data shown in FIG. 5A are the means of the clinical scores (based on percent weight changes, diarrhea, stool watering and bleeding) in each group (n=8-10) and are representative of three separate experiments. In the absence of MDSCs, treatment of GA, SP600125, or both did not significantly lower the clinical score of treated mice (FIG. 5A). Treatment of MDSCs alone decreased the clinical manifestations of IBD in treated mice. In combination with GA and SP600125, adoptive transfer of MDSCs further decreased the IBD clinical score in the treated mice. Importantly, the scores of these mice were not statistically different from naive healthy mice throughout the entire duration of the experiment. The double blind pathological score was also diagnosed, by professional IBD pathologists, and the results are shown in FIG. 5B. In combination with GA and SP600125, adoptive transfer of MDSCs significantly decreased the IBD pathology score in the treated mice (FIG. 5B).

Figure 5C:
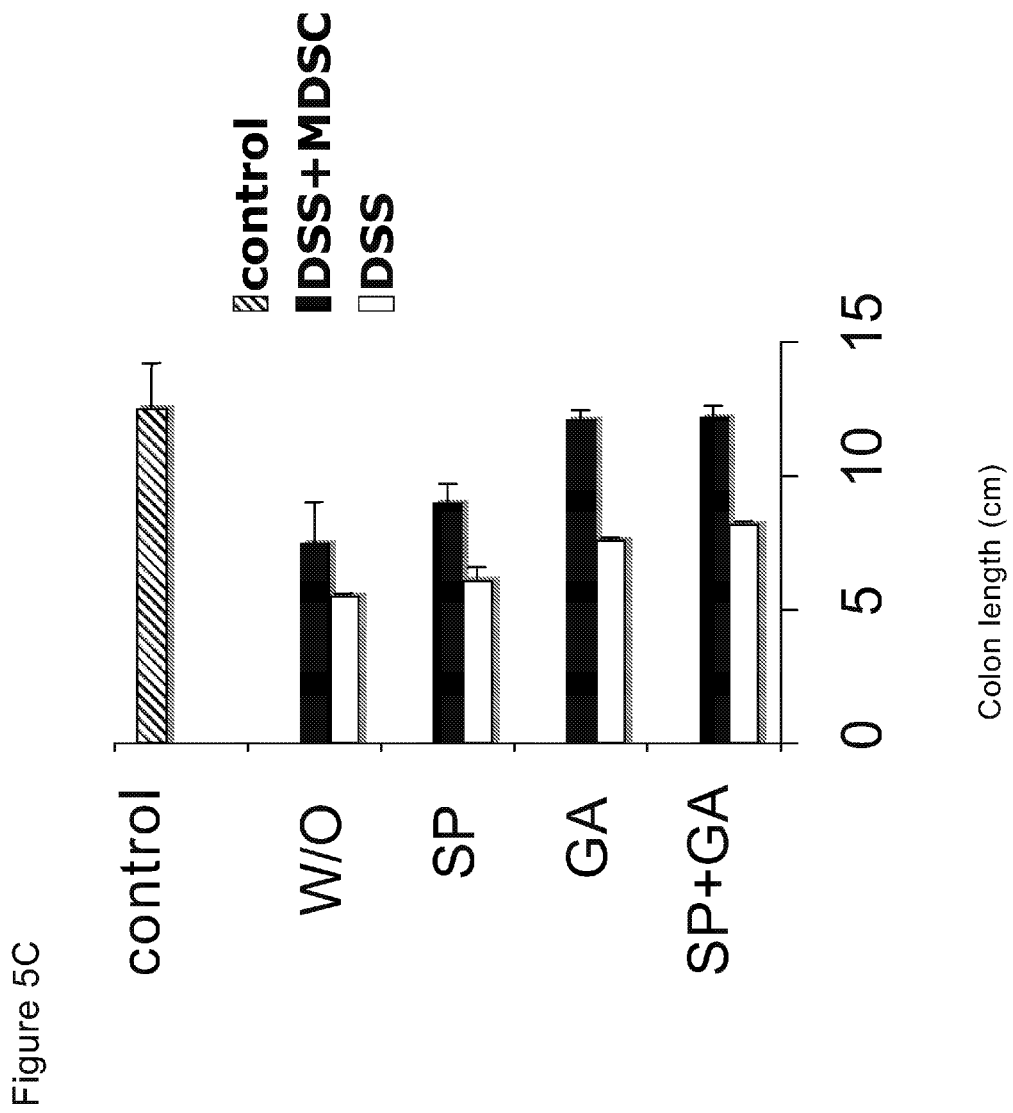
FIG. 5C. Graph quantifying colon lengths (cm) in indicated groups of mice with DSS-induced colitis treated with SP, GA, or SP+GA and control groups.

The reduction of colon length, an additional macroscopic manifestation of DSS-induced colitis, was also assessed. At day 11, colons were obtained from the treatment groups. Data are presented as the mean±SEM length of colon in each group (FIG. 5C). As shown in FIG. 5C, 55.2%, 51.6%, 45%, and 46.7% decreases in colonic length were observed in untreated SP600125-, GA-, and SP600125+GA-treated mice, respectively. In contrast, a reduction of 33% was observed in the mice treated with MDSCs alone. Mice treated with MDSCs in combination with SP600125, GA, or both showed 27%, 10.4% and 9.5% reductions, respectively, in comparison with naive healthy mice.

Figure 5D:
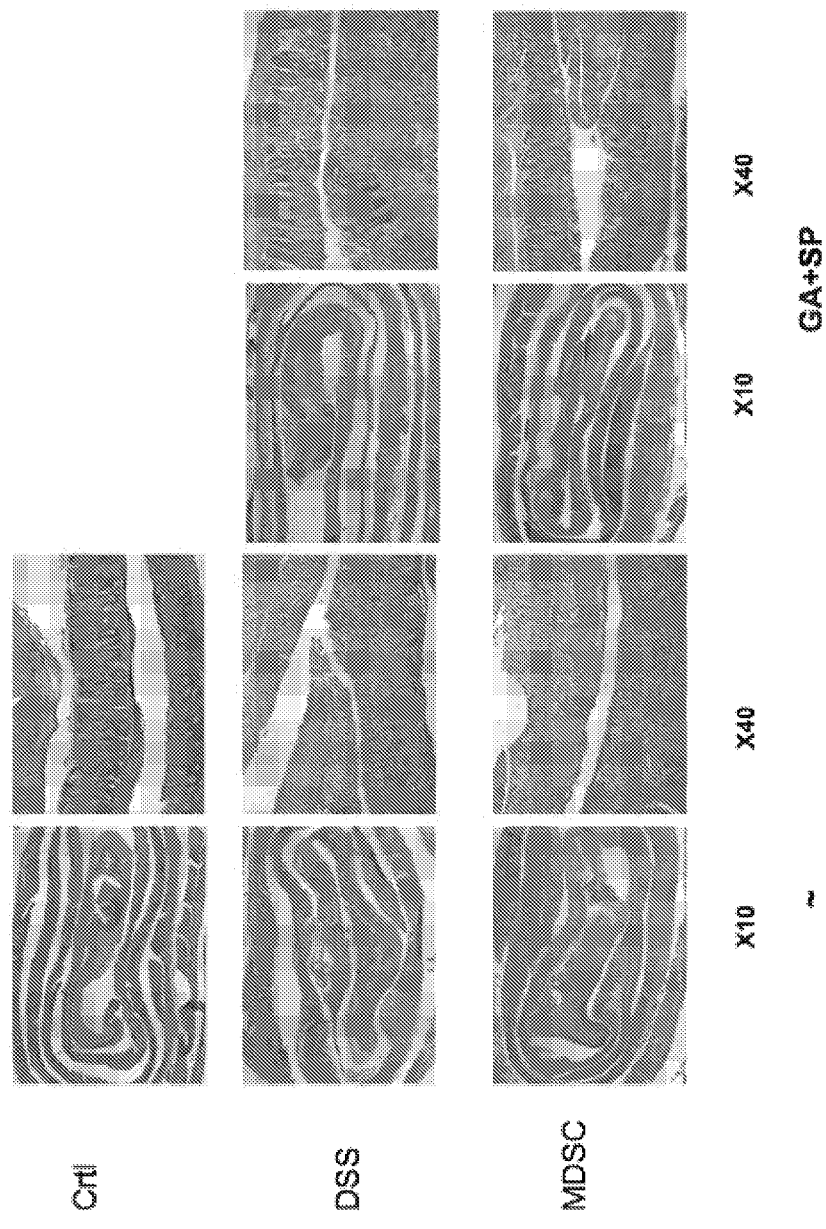
FIG. 5D. Histological analysis of colons from indicated treatment groups. Magnification is indicated below each column.

Histological assessment of colonic damage was performed in a double-blind fashion. On day 11 after IBD induction, severe infiltration of inflammatory cells such as neutrophils and lymphocytes in the mucosa, submucosa, and in some cases extending through all intestinal layers (transmural inflammation), as well as crypt destruction in the colon were observed in untreated mice. The average histological score was 1.75 on a scale of 0-4 (FIG. 5D). In the mice treated with MDSCs alone, less damage and more conserved glandular structure were revealed with an average histological score of 1.485, although mucosal and submucosal leukocyte infiltrations were found. In the treatment group that received MDSCs in combination with single small compound, SP600125 or GA or combination, the average histological scores were 1.1, 0.61, and 0.84, respectively. Importantly, the mice treated with MDSCs in combination with SP600125 plus GA did not show significant pathological manifestation, with an average histological score of 0.23, and were similar to naïve untreated mice in all the parameters tested.

The cytokine profiles in the colons of treated mice were analyzed. On day 11 after IBD, colons were removed and processed to determine the concentration of IFN-γ, IL-17A, IL-10, and TGF-β. MDSC administration led to a reduction in the levels of IFN-γ (386.87±10 pg/mL) and IL-17A (56.24±4.2 pg/mL) when compared with the untreated DSS-IBD-induced mice (IFN-γ (106.41±13 pg/mL) and IL-17A (37.50±4 pg/mL)) (FIG. 6A) and an increase in the levels of TGF-β (201.42±14 vs 98.62±10 pg/mL) and IL-10 (422.92±145.63 vs 11.99±2.3 pg/mL, FIG. 6B).

Figure 6A:
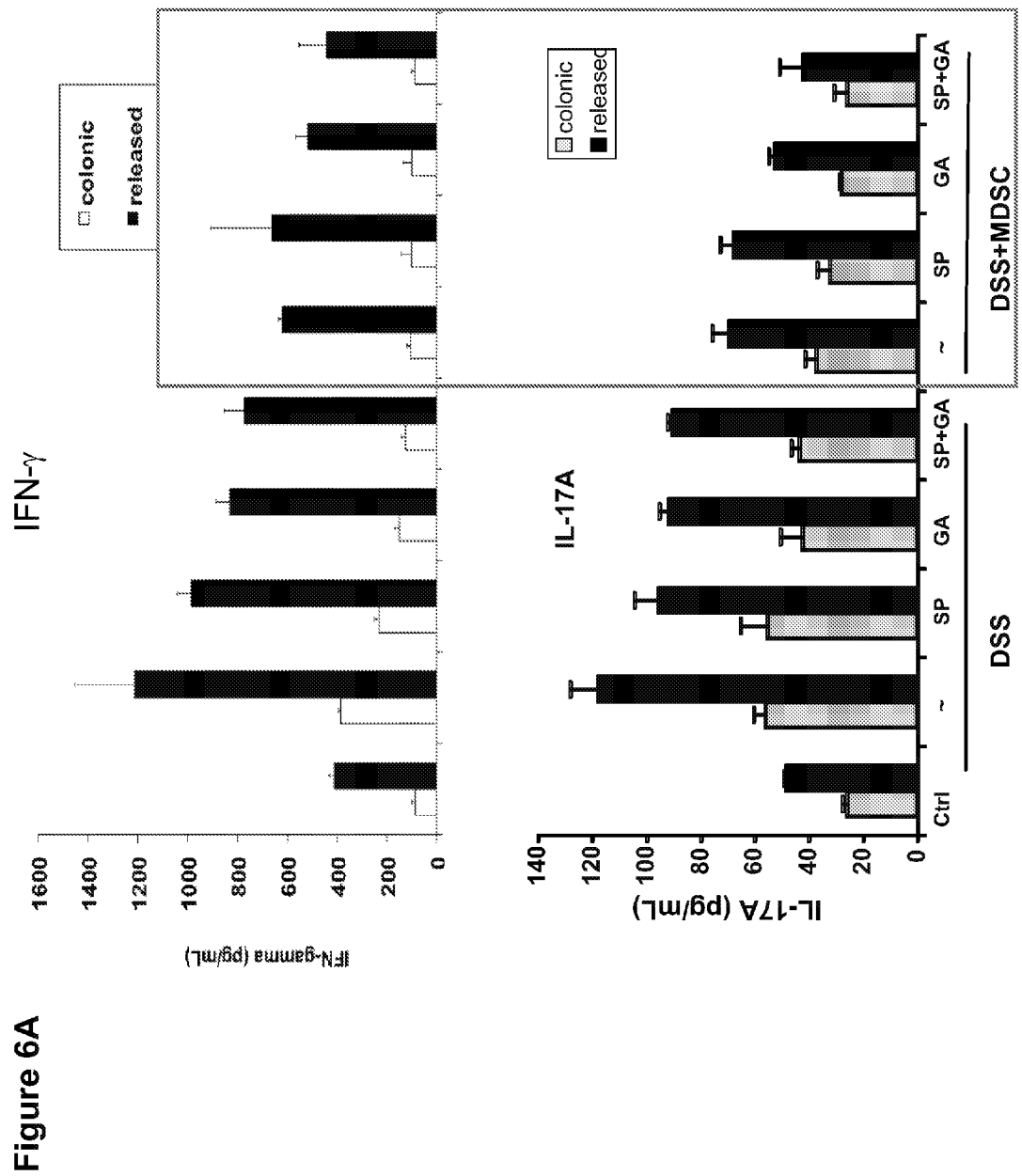
FIG. 6A. Bar graph showing that MDSCs and treatment with small compounds decrease pro-inflammatory cytokine (IFN-γ, IL-17A) production in colon tissue from DSS induced IBD mice.
Figure 6B:
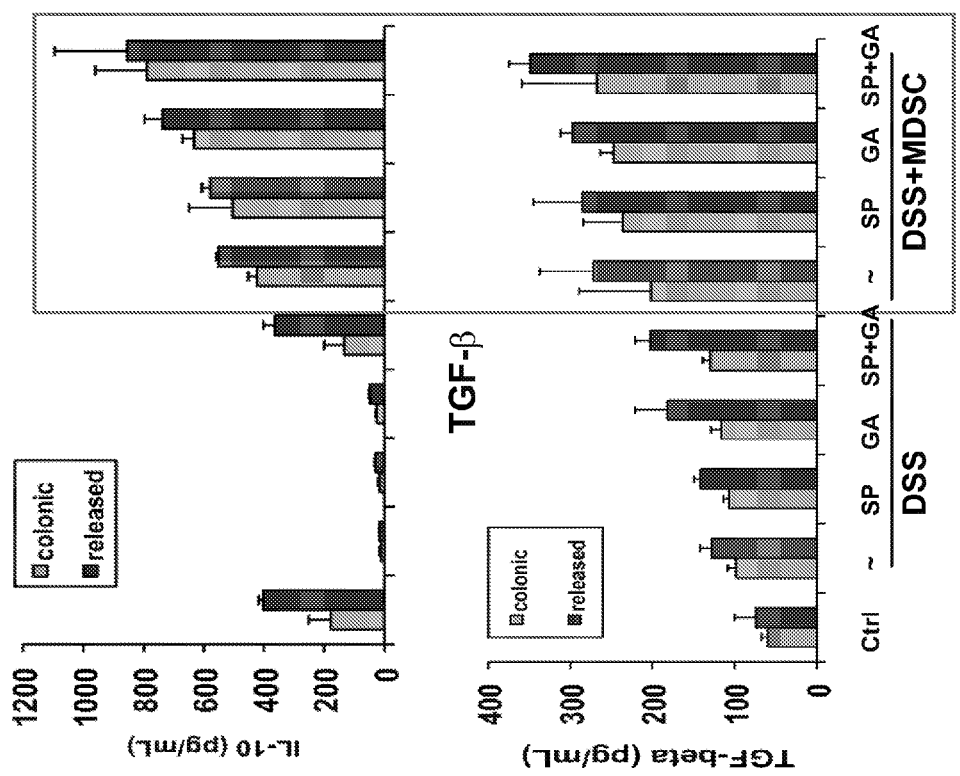
FIG. 6B. Bar graph showing MDSCs and small compounds treatment enhance anti-inflammatory cytokine (IL-10, TGF-β) production in colon tissue from DSS induced IBD mice.

Additionally, colon segments of the same location from various experimental groups were isolated and incubated for 24 hours, and the concentrations of released cytokines in the supernatant were measured. As shown in FIG. 6A, MDSC treatment resulted in a significantly lower production of IFN-γ (620.3042±79.7 vs 1211.57±109.41 pg/mL) and IL-17A (69.53±1.76 vs 117.97±10 pg/mL) and higher production of TGF-β (272.15±65 vs 128.11±88 pg/mL) and IL-10 (551.5±7.77 vs 11.99±2.3 pg/mL) when compared to the untreated DSS-IBD-induced mice. The combination of SP600125 and GA with MDSC administration synergistically decreased colonic IL-17A or IFN-γ production, and increased colonic IL-10 and TGF-β production.

These results demonstrate that the administration of MDSCs into the IBD mice induces the production of IL-10 and TGF-β and inhibits the expression of IFN-γ and IL-17A in colon, presumably resulting in the switch from a Th1- or Th17- to a Th2- or Treg cell-mediated immune response. Further, these results demonstrate that the combination of GA and SP600125 had a synergistic effect for reducing the symptoms of IBD.

Figure 7:
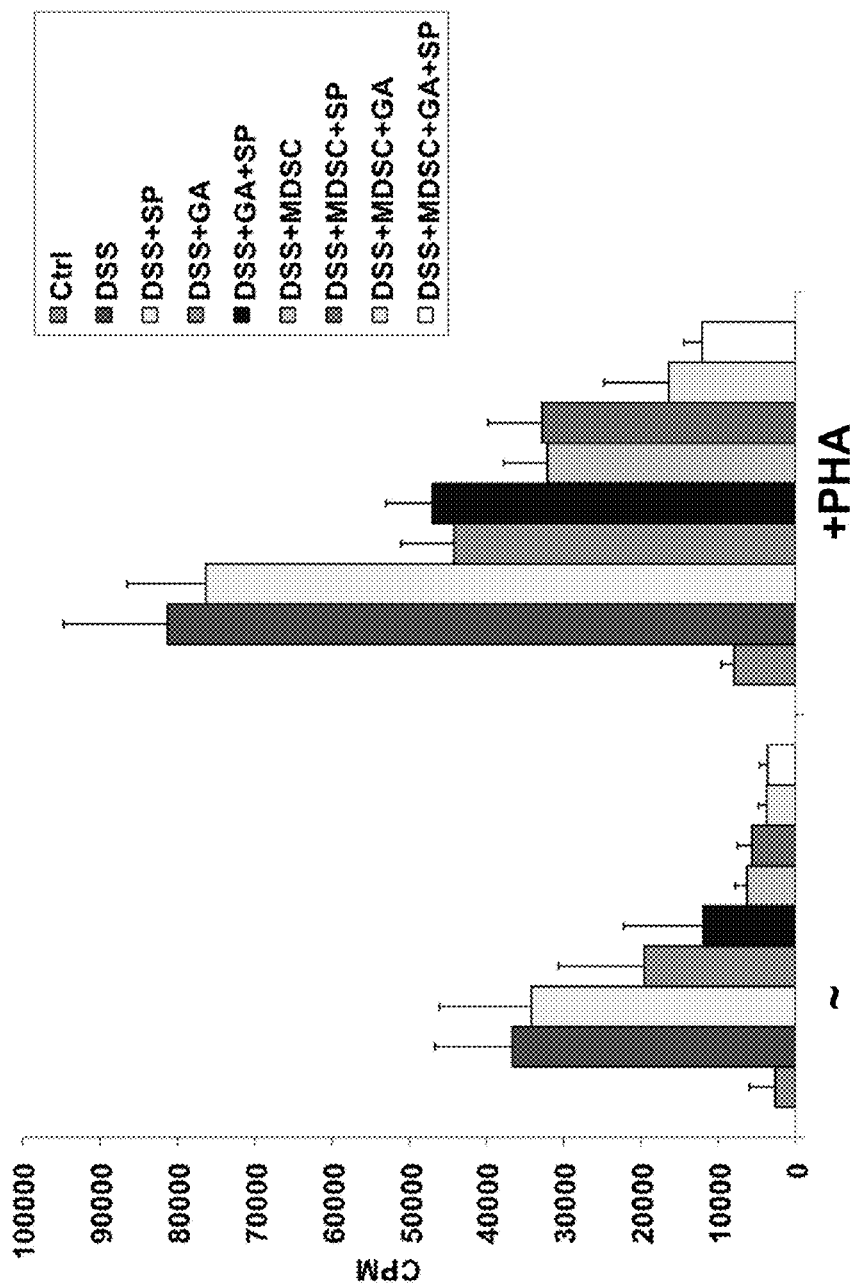
FIG. 7. Bar graph quantifying proliferative responses of mesenteric lymph node (MLN) cells isolated from IBD mice after indicated treatments. CPM is counts per minute and PHA is phytohaemagglutinin.
Figure 8:
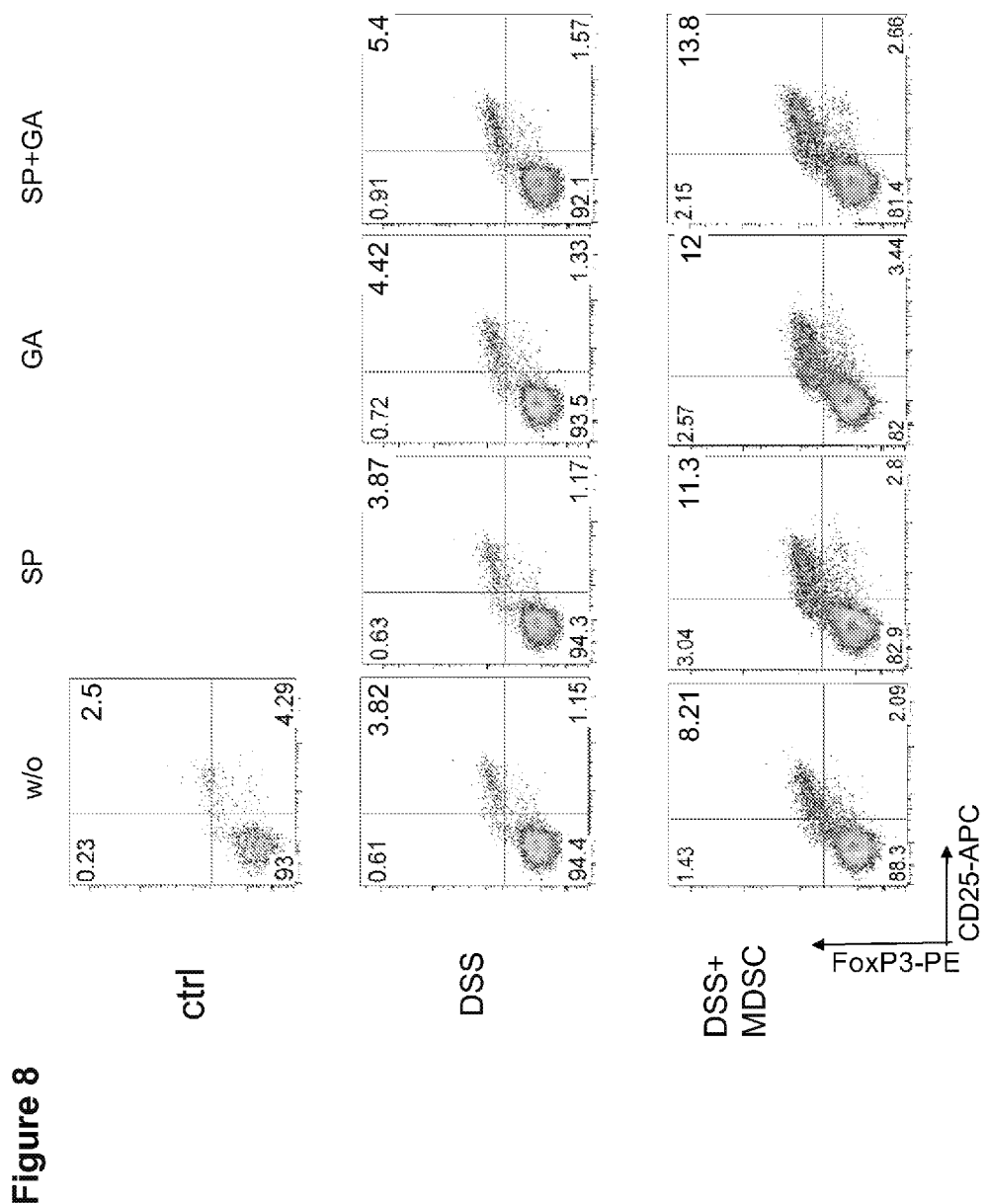
FIG. 8. Flow cytometric data expressed in cell plots showing the presence of Treg cells in MLN of mice with DSS-induced colitis or wild type ("WT") mice that were treated with the indicated combinations of MDSCs, SP600125 and GA or without treatment ("w/o").

To assess the proliferative capability of T cells from treated mice, on day 11 following IBD induction, splenocytes and mesenchymal lymph node (MLN) cells from treated mice were stimulated with (+PHA) or without PHA (~) for 72 hours. [3H]-thymidine was pulsed during the last 8 hours of 72-hour culture. As shown in FIG. 7, a lower level of T-cell proliferation in +PHA groups was observed in the MLN of GA-treated, GA+SP600125 (SP)-treated, and MDSCs-treated mice that had been treated with DSS. Surprisingly, MLN T cells from DSS-treated mice treated with MDSCs+ SP+GA exhibited hypo-proliferative responses, and the T cell responses were significantly more reduced compared to MDSCs+GA or MDSCs+SP. The hypo-proliferation was not as significant in the splenic T cells, suggesting a local immune suppression of inflammatory response by MDSCs. The presence of CD4+CD25+Foxp3+ Treg cells in MLN was also determined MLN cells were isolated and stained with anti- CD4-FITC+anti-CD25-APC+anti-Foxp3-PE or isotype controls followed by flow cytometric analysis. The percentage of Treg cells is defined as the percent cells that are stained positive for CD4, CD25, and intracellular Foxp3. A highest percentage of Treg cells in the MLN was detected in the treatment group that received MDSCs+GA+SP600125 (FIG. 8).

EXAMPLE 4

GA Regulates the Suppressive Function of MDSCs Through TLR Pathways

Figure 9A:
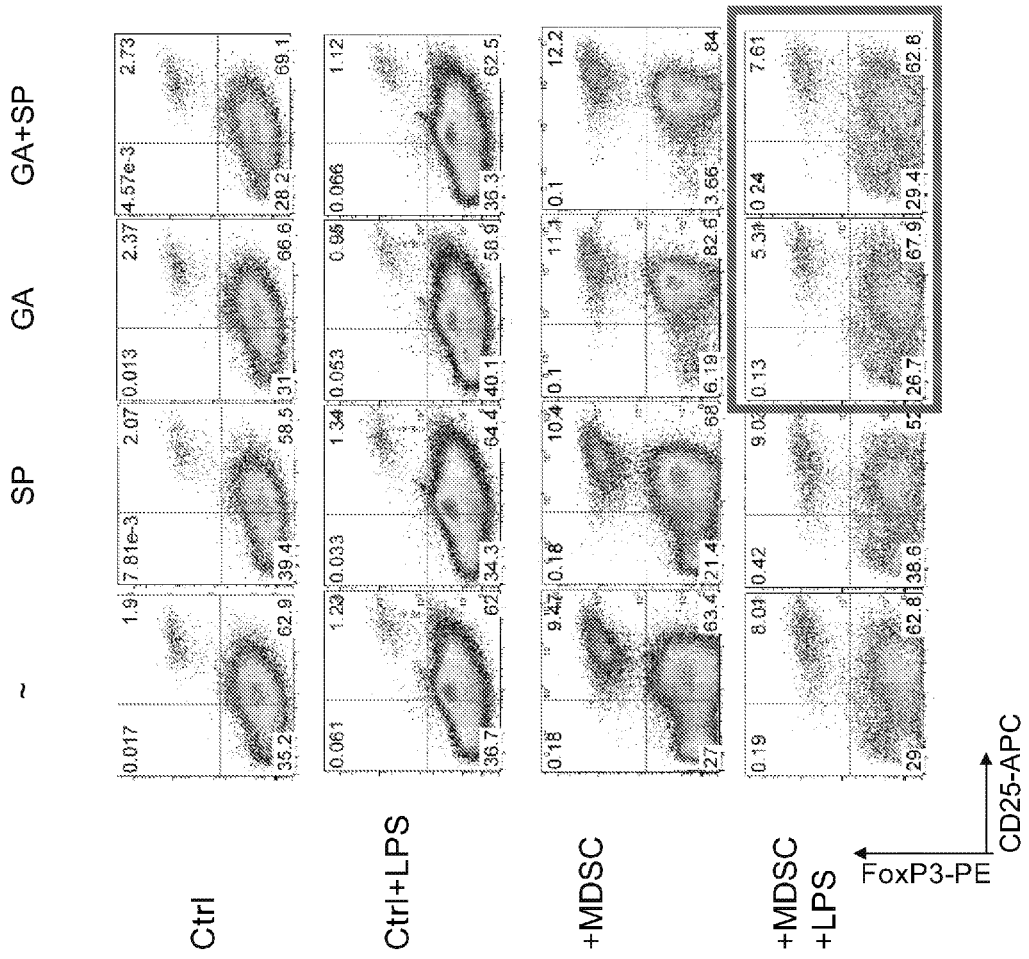
FIG. 9A. Flow cytometric data expressed in cell plots showing that GA-mediated enhancement of Treg cell inducing activity by MDSCs is abrogated by LPS. Treg cells are double positive for FoxP3 (Y-axis) and CD25 (X-axis).

The molecular mechanism underpinning the modulation of MDSC suppressive functions by GA was investigated. Based on the results from microarray analysis, GA treatment of MDSCs resulted in a significant reduction of the levels of TLR 2, 3, and 4 expression, showing that GA can enhance the suppressive functions of MDSCs by suppressing TLR signaling in MDSCs. It was further tested whether LPS (a TLR4 ligand) can abrogate the effect of GA on MDSCs. CD4+ HA TCR transgenic splenocytes were co-cultured with irradiated MDSCs in the presence or absence of GA, SP600125 or both ±LPS (100 ng/mL). Five days later, cells were harvested and stained with anti-CD4-FITC+anti-CD25-APC+anti-Foxp3-PE or isotype controls followed by flow cytometry. Treatment of LPS slightly decreased the Treg cell inducing activity of MDSCs (from 9.47% to 8.01%). GA- and GA+SP600125-mediated enhancement of Treg cell induction by MDSCs was substantially abrogated by LPS treatment (from 11.1% to 5.31% and from 12.2% to 7.61%, respectively; FIG. 9A).

Figure 9B:
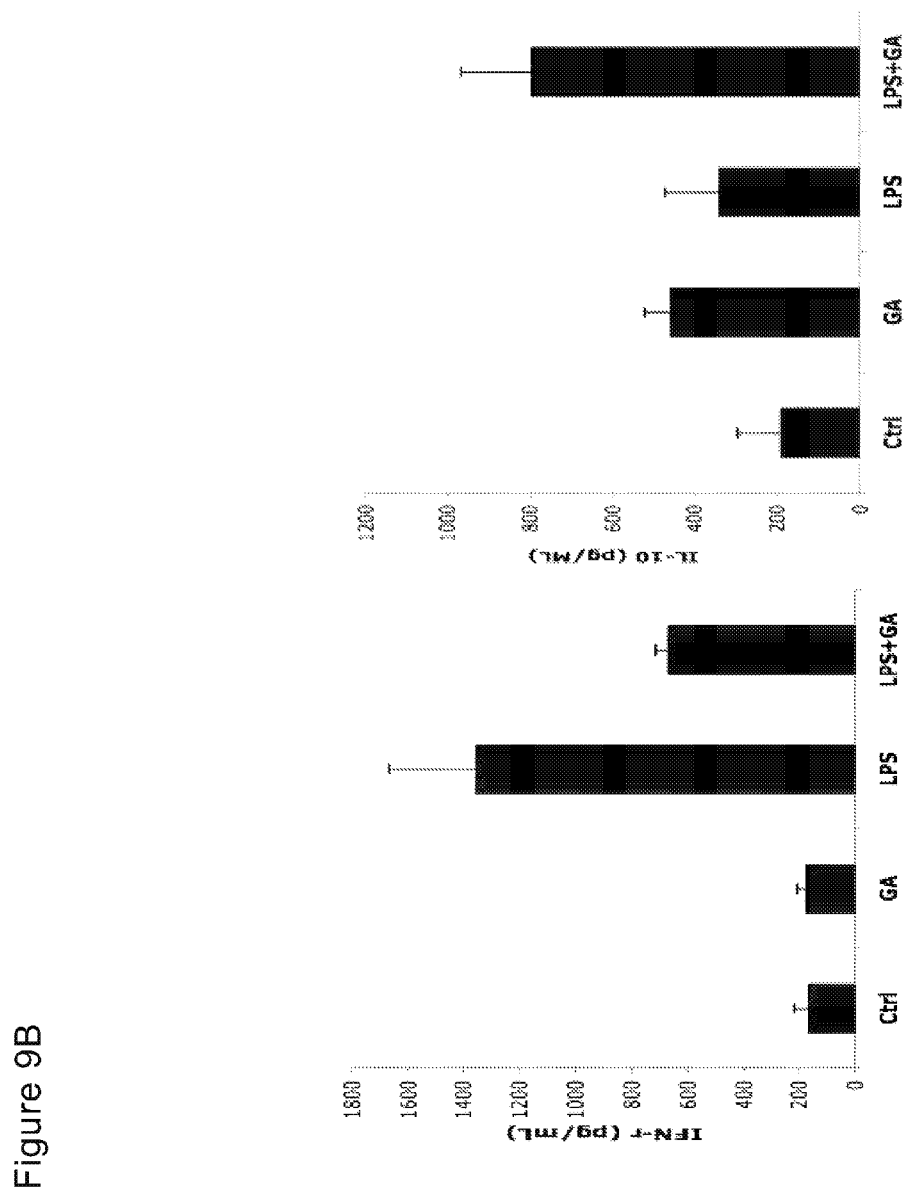
FIG. 9B. Bar graphs quantifying MDSC cytokine production in the presence of the indicated small compounds and LPS. Graphs show that GA inhibits Th1 cytokine production and favors IL-10 production by MDSCs.

CD115+ MDSCs from bone marrow were isolated and cultured in complete media plus 100 ng/mL LPS with or without GA for 30 hours. IL-10 and IFN-γ levels in the supernatant were measured by ELISA. IL-10 level was further enhanced in the presence of LPS, but more interestingly, the IFN-γ production induced by LPS was significantly reduced by GA stimulation (FIG. 9B). The result shows that GA can counteract the effect of TLR4 signaling, resulting in the suppression of Th1 function and favoring Th2 response.

Figure 9C:
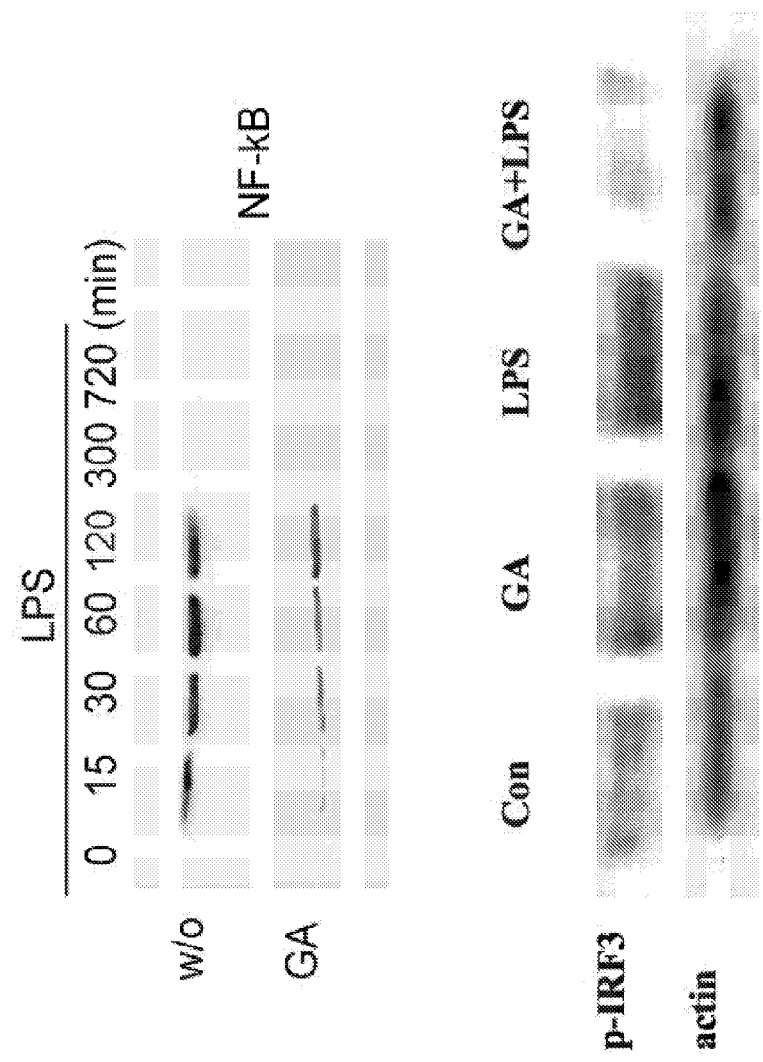
FIG. 9C. Western blot showing that GA downregulated phosphorylated NF-κB and IRF-3 levels in MDSCs stimulated with LPS for 2 hours. Actin was used as a loading control.

The effect of GA on the components (NF-κB and IRF-3) of the TLR4-LPS signaling pathway was analyzed by Western blot analysis of protein samples from MDSCs stimulated with LPS for 2 hours. As shown in FIG. 9C, GA treatment resulted in the inhibition of NF-κB and IRF-3 activation induced by LPS.

Figure 9D:
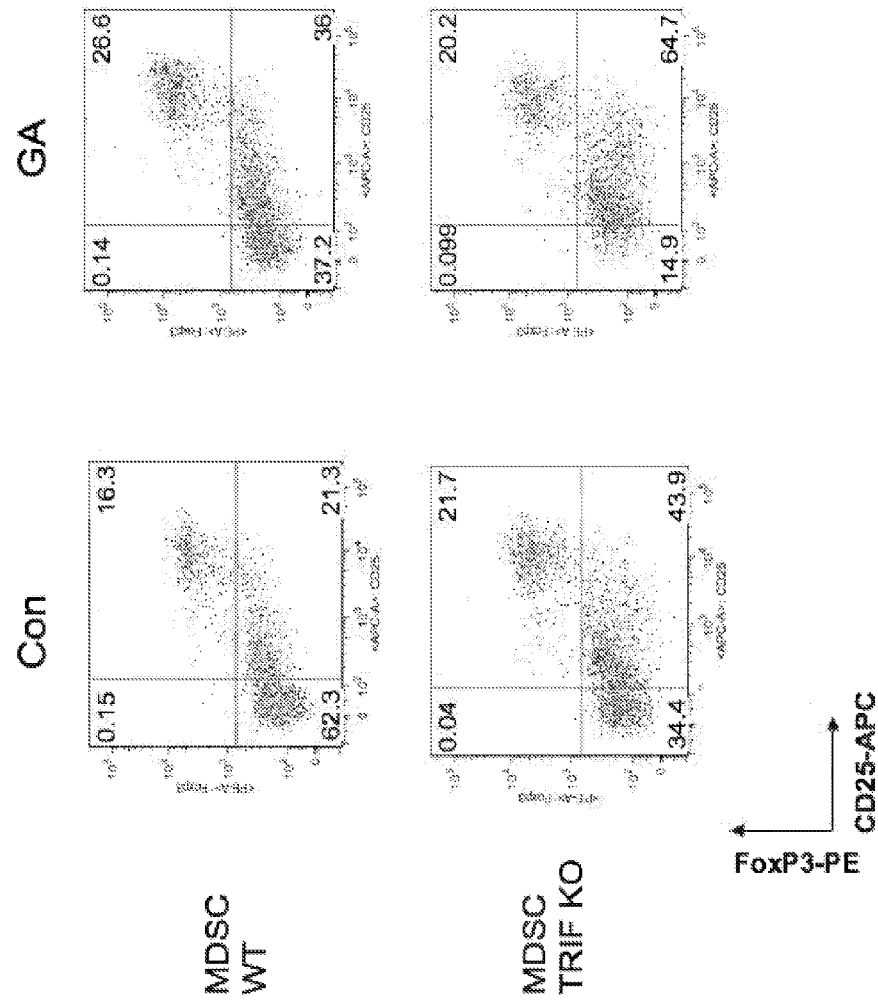
FIG. 9D. Flow cytometric data expressed as cell plots showing Treg cell induction by MDSCs derived from wild type ("WT") or TRIF knockout (KO) mice in the presence of OVA peptide and CD4 OVA TCR transgenic splenocytes following treatment with or without GA.

To determine whether the effect of GA on MDSC-driven Treg cell induction is dependent on the MyD88 independent (TRIF) pathway (used by TLR4 and TLR3), TRIF KO mice were used. TRIF is upstream of IRF-3. MDSCs derived from wild type or TRIF KO mice were cultured in the presence of OVA peptide and CD4 OVA TCR transgenic splenocytes for 5 days. Cells were stained with primary antibody specific for Foxp3, CD4 and CD25 and analyzed by flow cytometry. The results indicate that GA cannot enhance MDSC-mediated Treg cell induction in the absence of TRIF, as shown on FIG. 9D. Therefore, GA regulates the suppressive function of MDSCs through a TRIF-dependent pathway.

These results show that the mechanism for the effect of GA on MDSC suppressive activity may involve both the MyD88-dependent (NF-κB) and MyD88-independent (TRIF) pathways.

EXAMPLE 5

Figure 10A:
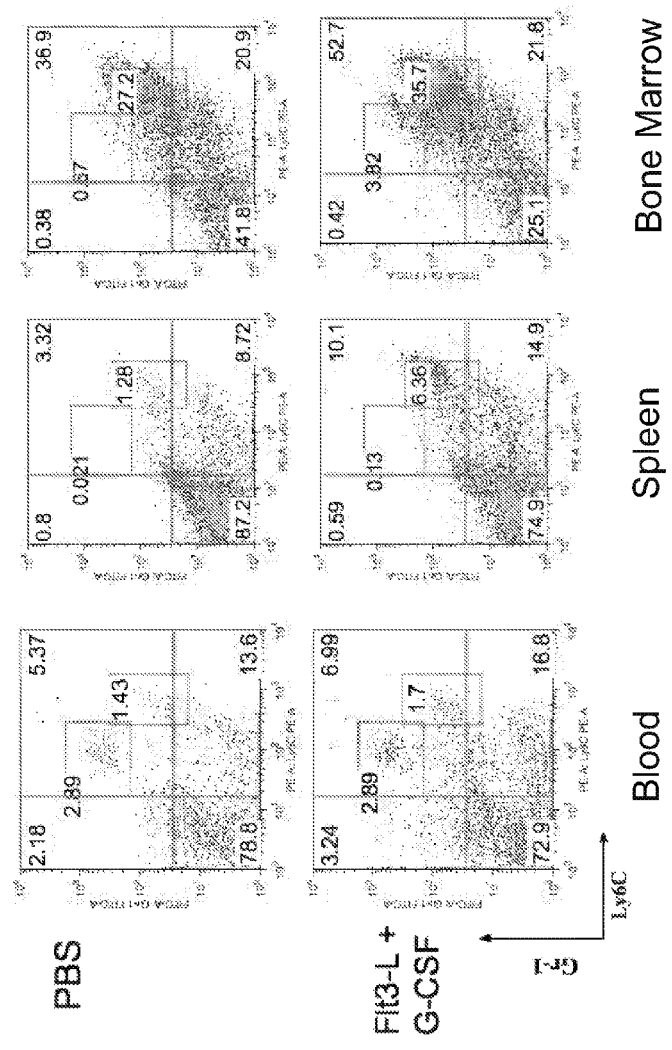
FIG. 10A. Flow cytometric data expressed as cell plots showing that MDSCs can be mobilized by treatment with Flt-3 Ligand and G-CSF. MDSCs are identified as Gr-1(low) (Y-axis) Ly-6C+ (X-axis) cells.

Endogenous MDSCs Induced by Mobilization of Bone Marrow Cells in Conjunction with Small Compound Treatment Prevents the Onset of IBD MDSC Mobilization can be Induced by the Treatment of Flt3-Ligand and G-CSF In Vivo To devise a clinically applicable means to increase and mobilize MDSCs into the periphery, it was determined whether Flt3 Ligand (Flt3-L) plus G-CSF could increase and mobilize MDSCs in the peripheral lymphoid organs. Mice were treated with PBS control or Flt3-L (2 µg/day) plus G-CSF (2 µg/day) for 5 consecutive days. The numbers of MDSCs in the blood, spleen, and bone marrow were quantified on day 7. The injection of Flt3-L and G-CSF resulted in a substantial increase of Gr-1(low)Ly-6C+ MDSCs in the peripheral blood, spleen and bone marrow of treated mice when compared to PBS-treated control mice (1.7% vs. 1.43% in blood, 6.36% vs. 1.28% in spleen, and 35.7% vs. 27.2% in bone marrow) (FIG. 10A). The results indicate that treatment of Flt3-L and G-CSF can increase MDSCs in the bone marrow and can mobilize MDSCs into the periphery.

Figure 10B:
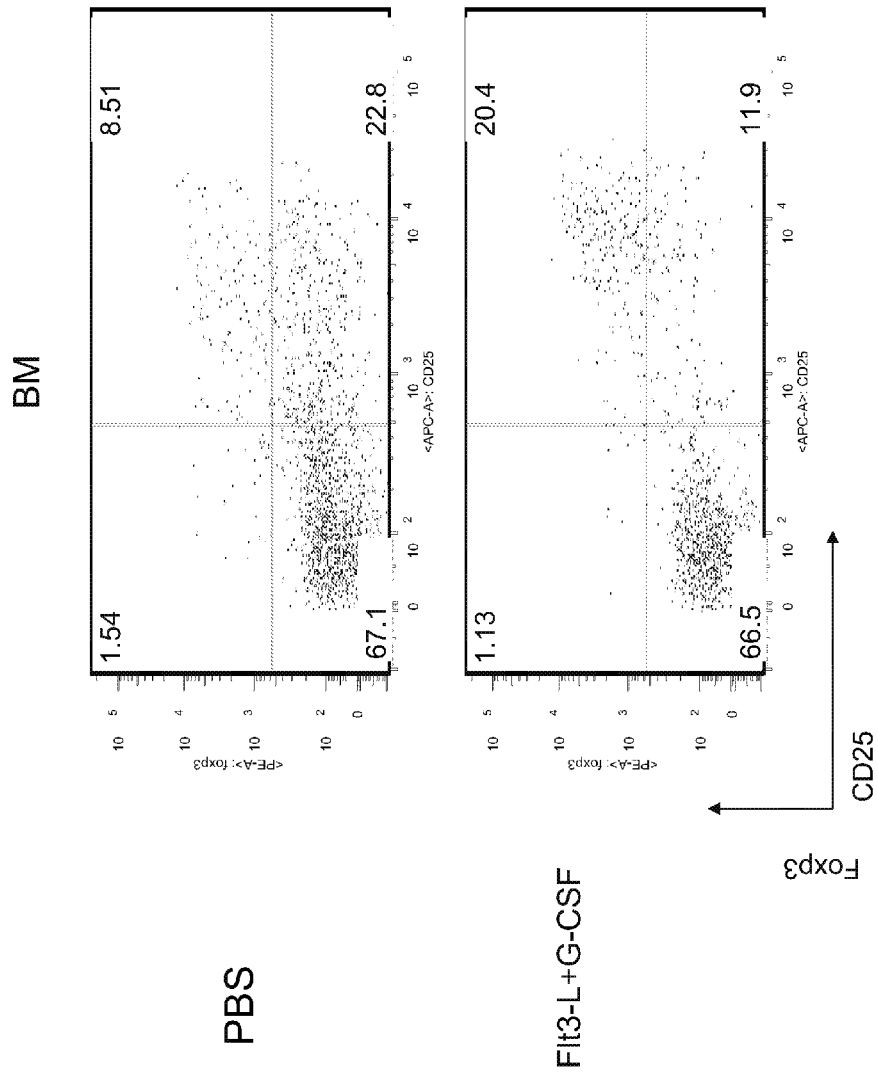
FIG. 10B. Flow cytometric data expressed as cell plots showing Treg cell induction mediated by MDSCs.
Figure 10C:
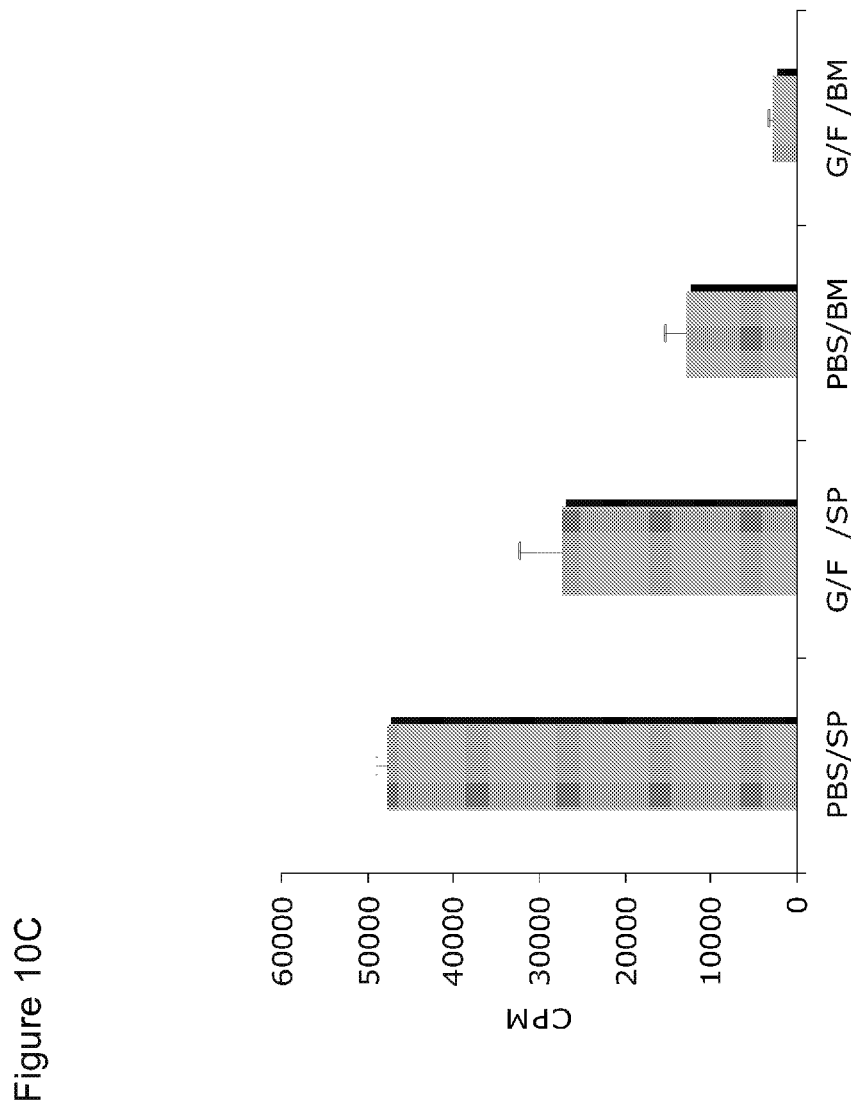
FIG. 10C. Bar graph showing MDSC-mediated suppression of T-cell proliferation induced by OVA. First bar (from the left): MDSCs from spleen of PBS-treated mice; second bar: MDSCs from spleen of Flt3-L+G-CSF-treated mice; third bar: MDSCs from bone marrow of PBS-treated mice; fourth bar: MDSCs from bone marrow of Flt3-L+G-CSF-treated mice.
Figure 11A:
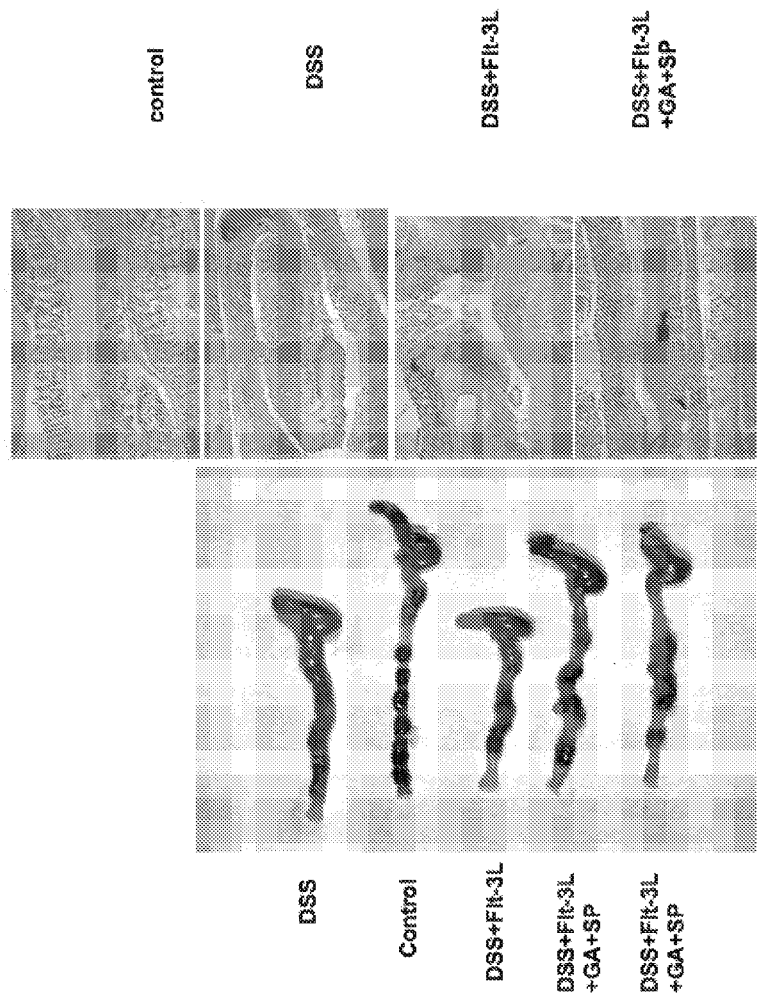
FIG. 11A. Gross appearance of colons from indicated treatment groups (left panel) and H&E stained colon tissue sections from indicated treatment groups (right panel).
Figure 11B:
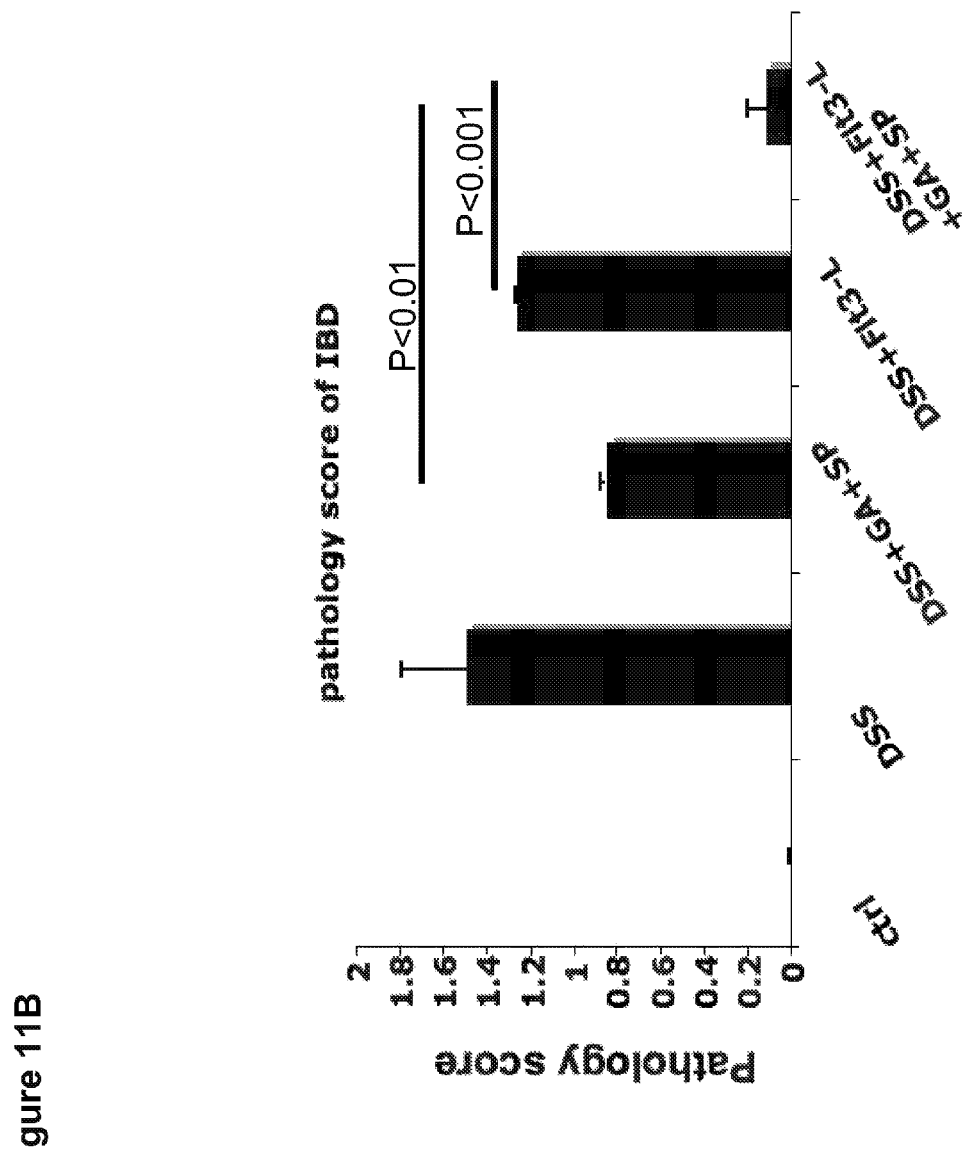
FIG. 11B. Bar graph quantifying IBD pathology scores of mice with DSS-induced colitis following treatment with or without the indicated combinations of MDSCs, GA, SP600125, and Flt3 Ligand.

It was next examined whether MDSCs mobilized by Flt3-L+G-CSF treatment had suppressive function. The sorted Gr-1(low)Ly-6C+CD115+ MDSCs from PBS-treated control mice or Flt3-L+G-CSF treated mice were co-cultured with CD4 OVA TCR transgenic splenocytes in the presence of OVA peptide for 5 days. The presence of Treg cells was assessed by staining with anti-CD4-FITC+anti-CD25-APC+anti-Foxp3-PE or isotype controls followed by flow cytometric analysis. A higher percentage of Treg cells was detected in the co-culture with MDSCs isolated from Flt3-L+G-CSF group when compared to those from PBS-treated mice (20.4% vs. 8.5%) (FIG. 10B). Next, isolated MDSCs were co-cultured with CD4 OVA TCR transgenic splenocytes at the ratio 1 to 4 in the presence of OVA peptide. [3H]-thymidine was added for the last 8 hours of 72-hour co-culture. MDSCs isolated from Flt3-L+G-CSF treated mice exhibited a stronger suppressive activity against T-cell proliferation when compared to the counterparts isolated from PBS-treated mice (FIG. 10C). These results demonstrated that treatment of Flt3-L and G-CSF can induce the expansion and mobilization of functionally suppressive MDSCs into the periphery. Mobilization of Endogenous MDSCs in Conjunction with Small Compound Treatment can Prevent IBD To further investigate whether cytokine-mobilized MDSCs prevent IBD, mice were treated with Flt3-L in conjunction with treatment of small compounds (GA and SP600125) followed by IBD induction by DSS. Mice were treated with Flt3-L (2 µg/day) or PBS for three days before IBD induction. On the same day of IBD induction and thereafter daily, mice were treated with PBS or small compounds. The clinical score assessment showed that the clinical symptoms of IBD were prevented in mice treated with Flt3-L plus small compounds. The colon length in Flt3-L plus small compound-treated group had nearly the same colon length as the healthy control group and no significant pathologic colon inflammatory lesions were observed in the treated group (FIG. 11A). The clinical scores were assessed in a double-blind fashion. The pathology score of IBD in Flt3-L plus small compound-treated mice was substantially lower than that of PBS-treated control group (0.12±0.08 vs. 1.49±0.3) (FIG. 11B). The result showed that the combination of small compound treatment (GA+SP600125) with cytokine (Flt3-L)-mediated MDSCs mobilization can have therapeutic potential for the treatment of IBD.

EXAMPLE 6

Overview of MDSC Activation Pathways Through MAP Kinase, NFkappaB and PI3Kinase

Figure 12:
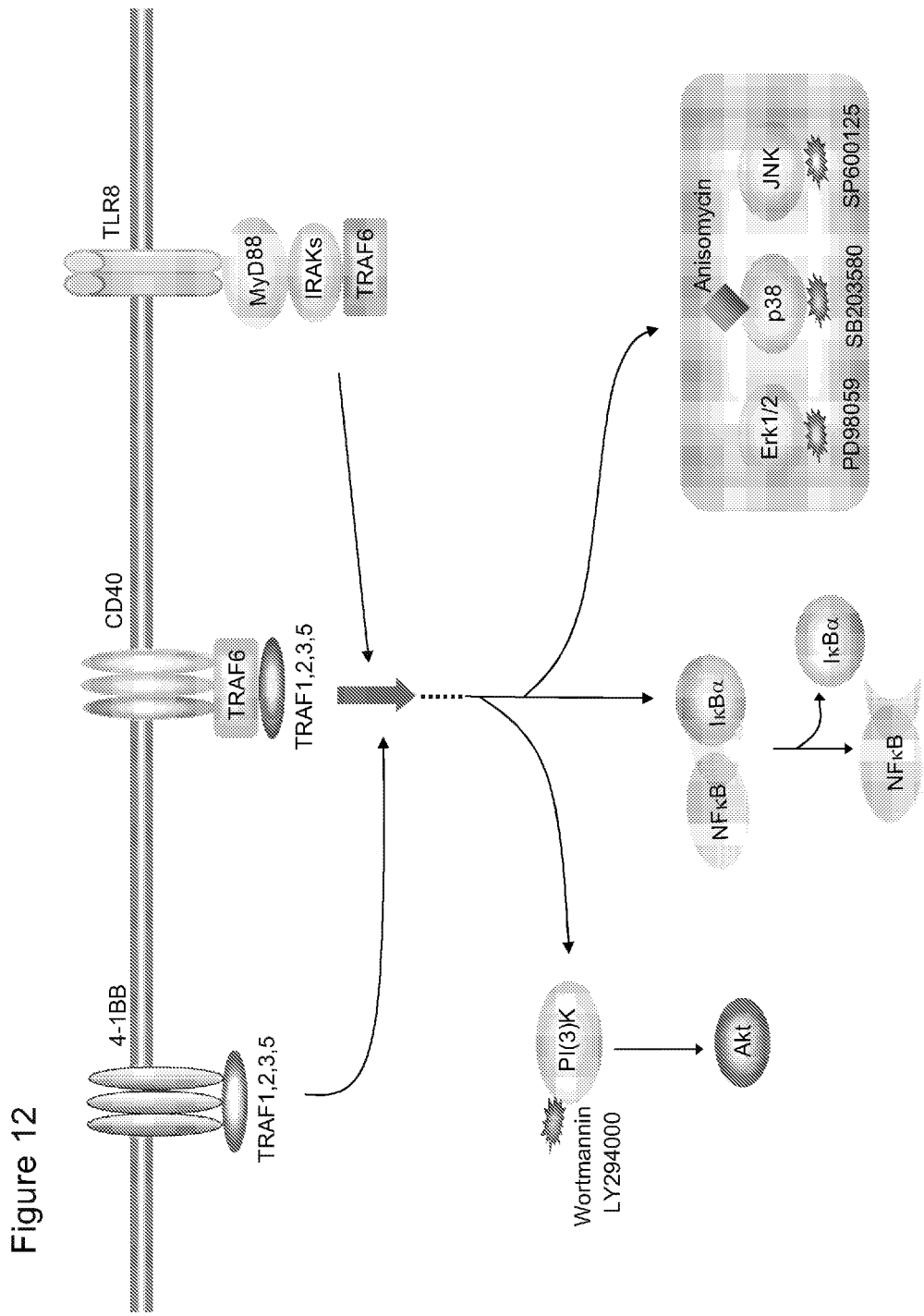
FIG. 12. Schematic diagram showing overview of MDSC activation through the MAP kinase, NFkappaB and PI3Kinase pathways and the pathway targets of various inhibitors (e.g., Wortmannin LY294000, Erk inhibitor PD98059, p38 MAP kinase inhibitor SB203580 and JNK inhibitor SP600125) and the MAP kinase activator anisomycin.

Since activation of TLR, CD40 or 4-1BB on MDSCs can reverse the immune suppression mediated by MDSCs, it was further hypothesized that blockade of downstream signaling pathways of MAP kinase, NFkappaB (NFκB) or PI3Kinase could enhance MDSC-mediated immune suppression. The targets in those pathways of inhibitors such as Erk inhibitor PD98059 (PD), p38 MAP kinase inhibitor SB203580 (SB), JNK inhibitor SP600125 (SP), PI3 kinase LY294000 and NFκB inhibitors (e.g., BAY117082, parthenolide, MG132, curcumin, arsenic trioxide, NFκB-p65 siRNA or dominant negative NFKapaB subunit e.g. p50) in these pathways, as well as the target of the MAP kinase activator, anisomycin, are shown in FIG. 12. While the inhibitors such as PD, SB, SP LY294000 and NFκB inhibitor, can enhance MDSC-mediated immune suppression, the activation of MAP kinase pathway, e.g., by anisomycin, may promote MDSC differentiation, thereby preventing MDSC-mediated immune suppression.

EXAMPLE 7

Figure 13A:
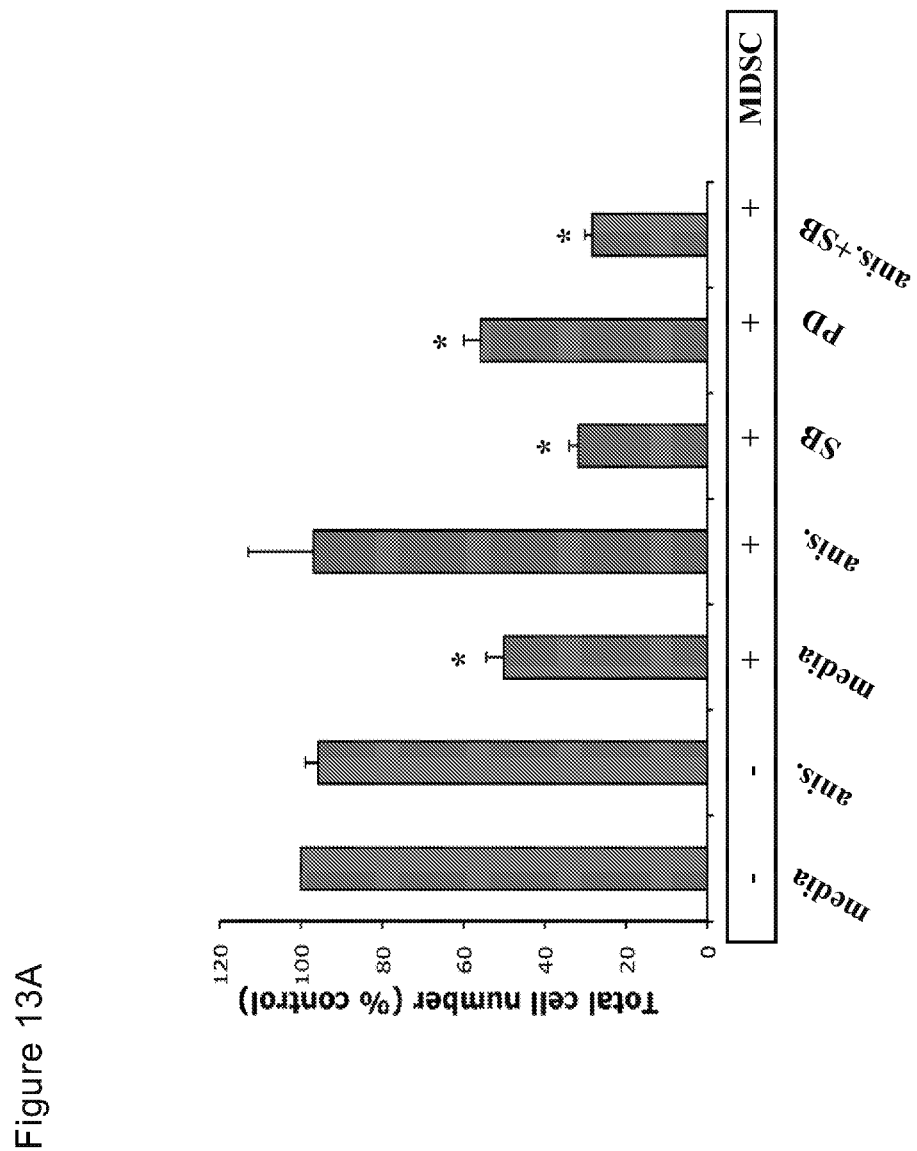
FIG. 13A. Graph showing HA-TCR T-cell proliferation in the presence of MDSCs, HA peptide, and, where indicated, anisomycin ("anis"), P38 inhibitor SB203580 ("SB"), and JUNK inhibitor PD98059 ("PD"). "Media" is the negative control (no addition of anisomycin, SB or PD).

Inhibition of MAP Kinase Enhances T Cell Suppression and Treg Activation by MDSCs To determine whether MAP kinase is involved in MDSC-mediated T cell suppression and Treg activation, monocytic MDSCs (Gr-1+/CD115+) were purified from spleen of tumor bearing mice and the suppressive function was evaluated. Purified T cells from HA-TCR transgenic T cells were cultured in the presence or absence of irradiated purified Gr-1+/CD115+ MDSCs from tumor-bearing mice, irradiated splenocytes from naïve mice as antigen presenting cells, anisomycin, various inhibitors, and HA peptide (0.5 µg/ml). Three days later, T cell proliferation was assessed by counting viable (trypan blue negative) total T cell number. Proliferation percentages were calculated by the number of experimental group divided by the number of T cell without MDSC, anisomycin or inhibitors (SB, PD). *$p<0.05$ by ANOVA t-test (FIG. 13A). As shown in FIG. 13A, MDSCs suppressed HA-TCR T-cell proliferation in response to HA peptide while the presence of anisomycin reverted the suppressive activity when compared to splenic MDSCs in the absence of anisomycin ($P<0.05$). However, the suppression was not reverted or enhanced by P38 inhibitor SB203580 and Erk inhibitor PD98059.

Figure 13B:
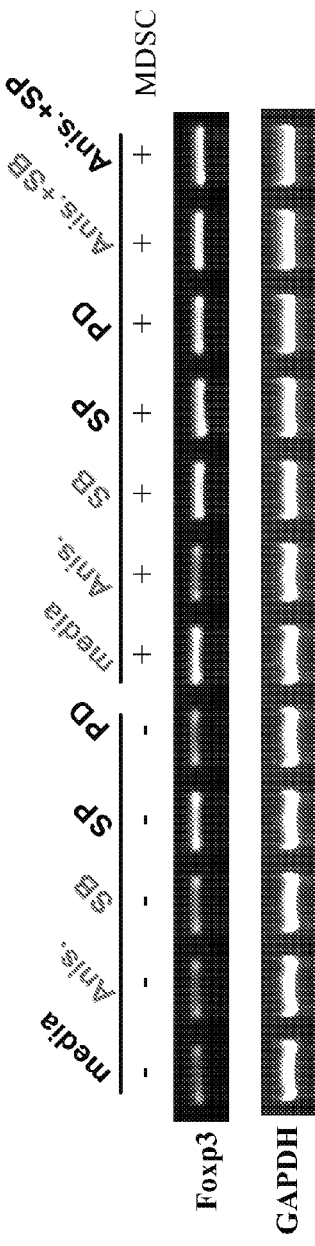
FIG. 13B. RT-PCR results showing expression of Foxp3 and GAPDH in HA-TCR T cells cultured in the presence of MDSCs, HA peptide, and, where indicated, anisomycin ("anis."), P38 inhibitor SB203580 ("SB"), and JUNK inhibitor PD98059 ("PD"). "Media" is the negative control (no addition of anisomycin, SB or PD).

The expression of Foxp3 and actin (as internal control) was determined by RT-PCR in MDSC-activated T regulatory cells in the presence of p38 MAP kinase activator, anisomycin, p38 MAP kinase inhibitor, SB, and Erk inhibitor, PD (FIG. 13B). MDSC-mediated Treg activation was significantly reverted in the presence of the p38 MAP kinase activator, but retained in the presence MAP kinase inhibitors. Treg induction by MDSCs was not significantly different between MDSCs in the absence or presence of MAP kinase inhibitors (e.g., SB, PD and SP) as assessed by Foxp3 expression by RT-PCR, whereas decreased Treg induction was observed in the presence of p38 MAP kinase activator anisomycin (FIG. 13B).

Discussion

In summary, the present Examples demonstrate that MDSCs exerted a stronger suppressive activity against T-cell proliferation and a stronger Treg cell inducing ability in the presence of GA or SP600125, and particularly, in the presence of both, in vitro. GA and SP600125 did not have any significant effect on normal monocytes isolated from naïve mice. Further study revealed that GA and SP600125 impeded the differentiation of MDSCs, thereby prolonging the suppressive phenotype and Treg cell-inducing ability of MDSCs. An increase in IL-10 and TGF-β production and a decrease in IL-6 and IL-23 secretion by MDSCs were observed in the presence of GA and SP600125. Furthermore, SP600125 and GA treated MDSCs suppressed IL-17A secretion by activated T cells.

Since SP600125 and GA enhanced the immunosuppressive functions of MDSCs, it was next determined whether MDSCs in combination with GA and SP600125 might be used for the treatment of IBDs using a model of DSS-induced IBD. The clinical scores, colon length reduction, and histological damage of the DSS-treated mice were significantly reduced by the treatment of MDSCs and the therapeutic effect of MDSCs was further enhanced by GA and SP600125. The combination of GA and SP600125 with MDSC administration was able to synergistically reduce IL-17A and IFN-γ production, and increase colonic IL-10 and TGF-β production. Importantly, a significant expansion of CD4+CD25+Foxp3+ Treg cells in mesenteric lymph node was observed in mice treated with MDSCs+GA+SP600125. In conclusion, JNK inhibitor SP600125 and GA had a surprising, synergistic effect for the treatment of IBD and enhanced the suppressive functions of MDSCs.

It was also demonstrated in the present examples that treatment of Flt3 ligand and G-CSF mobilized and increased MDSCs in the periphery. Mobilized endogenous MDSCs, in conjunction with treatment of GA and SP600125, prevented the onset of DSS-induced colitis. These results indicate that small compounds, such as GA and SP600125, can be used to modulate the suppressive functions of autologous mobilized MDSCs for the treatment of IBDs. In particular, it is presently discovered that the specific combination of GA and SP600125 is surprising better than using either inhibitor alone, for treating IBDs, and for inducing suppressive, Treg-inducing MDSCs. This discovery is not limited to IBDs, and is also useful for the treatment of autoimmune disease, allo-GVHD and organ transplantations, since all of these diseases would benefit from the action of suppressive MDSCs and the induction of Treg cells.

Further, it is to be understood that the invention is not limited only to GA and SP60015. These inhibitors are representative of classes of inhibitors that can be used to achieve the same effect—the treatment of the diseases and conditions described herein. For example, derivatives of GA, such as GA having amino acids substitutions or other modifications, may also be used in place of GA. Further, SP600125 is a MAP kinase inhibitor. The skilled artisan will readily understand that many MAP kinase inhibitors are readily available, and that any of these MAP kinase inhibitors may be used to achieve the same effect as SP600125.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A method for suppressing a T-cell-mediated pro-inflammatory immune response in a mammal, which comprises administering to a mammal in need of such treatment an effective amount for suppressing the T-cell-mediated immune response of:
   (i) a myeloid derived suppressor cell (MDSC); and
   (ii) glatiramer acetate (GA);
   wherein the MDSC is an immunosuppressive cell capable of suppressing antigen-specific T cell proliferation and inducing Foxp3+ T regulatory cells.

2. The method of claim 1, wherein the T-cell-mediated pro-inflammatory immune response is an alloimmune response.

3. The method of claim 1, further comprising administering to the mammal the small compound MAP kinase inhibitor SP600125.

4. The method of claim 1, wherein the mammal is a human.

5. A method for treating an autoimmune disease associated with an antigen-specific T cell response, which comprises administering to a mammal in need of such treatment an effective amount for treating the autoimmune disease of:
   (i) a MDSC, and
   (ii) GA;
   wherein the MDSC is an immunosuppressive cell capable of suppressing antigen-specific T cell proliferation and inducing Foxp3+ T regulatory cells.

6. The method of claim 5, wherein the autoimmune disease is selected from the group consisting of coeliac disease, type I diabetes, multiple sclerosis, thyroiditis, Grave's disease, systemic lupus erythematosus, scleroderma, psoriasis, arthritis, rheumatoid arthritis, alopecia greata, ankylosing spondylitis, Churg-Strauss Syndrome, autoimmune hemolytic anemia, autoimmune hepatitis, Behcet's disease, Crohn's disease, dermatomyositis, glomerulonephritis, Guillain-Barre syndrome, inflammatory bowel disease (IBD), lupus nephritis, myasthenia gravis, myocarditis, pemphigus/pemphigoid, pernicious anemia, polyarteritis nodosa, polymyositis, primary biliary cirrhosis, rheumatic fever, sarcoidosis, Sjogren's syndrome, ulcerative colitis, uveitis, vitiligo, and Wegener's granulomatosis.

7. The method of claim 5, further comprising administering to the mammal wherein the small compound MAP kinase inhibitor SP600125.

8. The method of claim 5, wherein the mammal is a human.

* * * * *